(12) United States Patent
Matthiesen

(10) Patent No.: US 10,202,638 B2
(45) Date of Patent: *Feb. 12, 2019

(54) COMPOSITIONS AND METHODS FOR PERFORMING HYBRIDIZATIONS WITH SEPARATE DENATURATION OF THE SAMPLE AND PROBE

(71) Applicant: Dako Denmark A/S, Glostrop (DK)

(72) Inventor: Steen Hauge Matthiesen, Hillerod (DK)

(73) Assignee: DAKO DENMARK A/S, Glostrup (DK)

( * ) Notice: Subject to any disclaimer, the term of this patent is extended or adjusted under 35 U.S.C. 154(b) by 212 days.

This patent is subject to a terminal disclaimer.

(21) Appl. No.: 15/096,036

(22) Filed: Apr. 11, 2016

(65) Prior Publication Data

US 2016/0304945 A1 Oct. 20, 2016

Related U.S. Application Data

(63) Continuation of application No. 13/203,160, filed as application No. PCT/IB2010/000659 on Feb. 26, 2010, now Pat. No. 9,309,562.

(51) Int. Cl.
*C12Q 1/68* (2018.01)
*C07H 21/00* (2006.01)
*C12Q 1/6841* (2018.01)
*C12Q 1/6832* (2018.01)

(52) U.S. Cl.
CPC ......... *C12Q 1/6841* (2013.01); *C12Q 1/6832* (2013.01); *C12Q 2527/125* (2013.01); *C12Q 2527/137* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 4,888,278 A | 12/1989 | Singer et al. | |
| 4,996,359 A | 2/1991 | Kesling, Jr. et al. | |
| 5,106,730 A | 4/1992 | Van Ness et al. | |
| 5,382,285 A | 1/1995 | Morrison | |
| 5,521,061 A | 5/1996 | Bresser et al. | |
| 5,525,492 A | 6/1996 | Hill | |
| 5,527,675 A | 6/1996 | Coull et al. | |
| 5,539,082 A | 7/1996 | Nielsen et al. | |
| 5,582,985 A | 12/1996 | Thompson | |
| 5,623,049 A | 4/1997 | Obberding et al. | |
| 5,633,129 A | 5/1997 | Karger et al. | |
| 5,705,333 A | 1/1998 | Shah et al. | |
| 5,714,331 A | 2/1998 | Buchardt et al. | |
| 5,718,915 A | 2/1998 | Virtanen et al. | |
| 5,736,336 A | 4/1998 | Buchardt et al. | |
| 5,750,340 A | 5/1998 | Kim et al. | |
| 5,766,855 A | 6/1998 | Buchardt et al. | |
| 5,773,571 A | 6/1998 | Nielsen et al. | |
| 5,786,461 A | 7/1998 | Buchardt et al. | |
| 5,837,459 A | 11/1998 | Berg et al. | |
| 5,869,237 A | 2/1999 | Ward et al. | |
| 5,891,625 A | 4/1999 | Buchardt et al. | |
| 5,925,744 A | 7/1999 | Haner et al. | |
| 5,972,610 A | 10/1999 | Buchardt et al. | |
| 5,986,053 A | 11/1999 | Ecker et al. | |
| 6,107,470 A | 8/2000 | Nielsen et al. | |
| 6,201,103 B1 | 3/2001 | Nielsen et al. | |
| 6,228,982 B1 | 5/2001 | Norden et al. | |
| 6,331,618 B1 | 12/2001 | Bloch et al. | |
| 6,357,163 B1 | 3/2002 | Buchardt et al. | |
| 6,475,720 B1 | 11/2002 | Gray et al. | |
| 6,555,670 B1 | 4/2003 | Aizawa et al. | |
| 6,656,685 B2 | 12/2003 | Utermohlen et al. | |
| 6,670,461 B1 | 12/2003 | Wengel et al. | |
| 6,794,499 B2 | 9/2004 | Wengel et al. | |
| 7,034,133 B2 | 4/2006 | Wengel et al. | |
| 7,374,945 B2 | 5/2008 | Becker | |
| 7,572,582 B2 | 8/2009 | Wengel et al. | |
| 7,750,208 B2 | 7/2010 | Huang et al. | |
| 7,867,443 B2 | 1/2011 | Key et al. | |
| 7,901,634 B2* | 3/2011 | Testa ...................... | B01L 3/508 422/547 |
| 8,034,909 B2 | 10/2011 | Wengel et al. | |
| 8,080,644 B2 | 12/2011 | Wengel et al. | |
| 8,153,365 B2 | 4/2012 | Wengel et al. | |
| 8,211,385 B2* | 7/2012 | Testa ...................... | B01L 3/508 422/547 |
| 8,632,739 B2* | 1/2014 | Testa ...................... | B01L 3/508 422/547 |
| 8,877,144 B2* | 11/2014 | Poulsen ............... | G01N 1/2813 422/509 |
| 9,133,507 B2* | 9/2015 | Testa ...................... | B01L 3/508 |
| 9,182,323 B2* | 11/2015 | Poulsen ............... | G01N 1/2813 |
| 9,297,035 B2* | 3/2016 | Matthiesen .......... | C12Q 1/6832 |
| 9,303,287 B2* | 4/2016 | Matthiesen .......... | C12Q 1/6832 |
| 9,309,562 B2* | 4/2016 | Matthiesen .......... | C12Q 1/6832 |
| 9,388,456 B2* | 7/2016 | Matthiesen .......... | C12Q 1/6832 |

(Continued)

FOREIGN PATENT DOCUMENTS

| EP | 1013772 A1 | 6/2000 |
|---|---|---|
| WO | 9102088 A1 | 2/1991 |

(Continued)

OTHER PUBLICATIONS

Toyozo, "Principal Assay Method in Infection Diagnosis, Chapter 3. Diagnosis of Infection by DNA Probe", Applied DNA Probe Technology, Feb. 5, 1998, 36-39.

(Continued)

*Primary Examiner* — Ethan C Whisenant

(57) ABSTRACT

The invention provides methods and compositions for separately denaturing a probe and target in hybridization applications. The invention may, for example, eliminate the use of or reduce the dependence on formamide in hybridization applications. Compositions for use in the invention include an aqueous composition comprising at least one polar aprotic solvent in an amount effective to denature doublestranded nucleotide sequences.

20 Claims, 2 Drawing Sheets

(56) References Cited

U.S. PATENT DOCUMENTS

| | | | |
|---|---|---|---|
| 2001/0000487 A1 | 4/2001 | Essenfeld et al. | |
| 2001/0007748 A1 | 7/2001 | An et al. | |
| 2001/0009766 A1 | 7/2001 | Bard et al. | |
| 2001/0010936 A1 | 8/2001 | Richards et al. | |
| 2001/0011131 A1 | 8/2001 | Luyten et al. | |
| 2001/0018512 A1 | 8/2001 | Blanchard | |
| 2001/0026919 A1 | 10/2001 | Chenchik et al. | |
| 2001/0027567 A1 | 10/2001 | Federoff | |
| 2001/0056203 A1 | 12/2001 | Sezi et al. | |
| 2002/0127569 A1* | 9/2002 | Weisburg | C12Q 1/6813 435/6.12 |
| 2002/0150904 A1 | 10/2002 | Bi et al. | |
| 2002/0164614 A1 | 11/2002 | Becker | |
| 2002/0182613 A1 | 12/2002 | Mirkin et al. | |
| 2002/0197629 A1 | 12/2002 | Gjerde et al. | |
| 2002/0198366 A1 | 12/2002 | Ashkenazi et al. | |
| 2003/0108903 A1 | 6/2003 | Wang et al. | |
| 2003/0175852 A1 | 9/2003 | Kalra et al. | |
| 2004/0029184 A1 | 2/2004 | Gourevitch | |
| 2004/0030093 A1 | 2/2004 | Sakurai et al. | |
| 2004/0048376 A1 | 3/2004 | Chabot et al. | |
| 2004/0053222 A1 | 3/2004 | Storhoff et al. | |
| 2004/0096967 A1 | 5/2004 | Gryseels et al. | |
| 2004/0210967 A1 | 10/2004 | Chen et al. | |
| 2004/0248790 A1* | 12/2004 | Hinuma | C07K 14/47 435/69.1 |
| 2004/0268439 A1* | 12/2004 | Cheng | C12N 9/00 800/282 |
| 2005/0014154 A1 | 1/2005 | Weizenegger | |
| 2005/0191657 A1 | 9/2005 | Demorest et al. | |
| 2005/0266459 A1 | 12/2005 | Poulsen et al. | |
| 2006/0030541 A1 | 2/2006 | Garcia et al. | |
| 2006/0147957 A1 | 7/2006 | Qian et al. | |
| 2007/0148657 A1 | 6/2007 | Myerson et al. | |
| 2007/0243545 A1 | 10/2007 | Kilpatrick et al. | |
| 2008/0044385 A1 | 2/2008 | Nishi et al. | |
| 2008/0227653 A1 | 9/2008 | Fodor et al. | |
| 2009/0123913 A1 | 5/2009 | Barany et al. | |
| 2009/0197346 A1 | 8/2009 | Winkler et al. | |
| 2009/0221429 A1 | 9/2009 | Fujimoto et al. | |
| 2009/0294305 A1 | 12/2009 | Bekki et al. | |
| 2011/0250698 A1 | 10/2011 | Pollner et al. | |
| 2011/0262930 A1 | 10/2011 | Deleersnijder et al. | |
| 2011/0281263 A1 | 11/2011 | Matthiesen et al. | |
| 2012/0331587 A1 | 12/2012 | Lassen et al. | |
| 2013/0017176 A1 | 1/2013 | Hosoda et al. | |
| 2013/0156695 A1 | 6/2013 | Sprecher et al. | |
| 2013/0230918 A1 | 9/2013 | Wakamiya | |
| 2017/0283805 A1* | 10/2017 | Bonci | C12N 15/1135 |

FOREIGN PATENT DOCUMENTS

| | | |
|---|---|---|
| WO | 9207956 A1 | 5/1992 |
| WO | 9402638 A1 | 2/1994 |
| WO | 9402639 A1 | 2/1994 |
| WO | 9604000 A1 | 2/1996 |
| WO | 9914226 A2 | 3/1999 |
| WO | 0069899 A1 | 11/2000 |
| WO | 0166804 A2 | 9/2001 |
| WO | 02061137 A2 | 8/2002 |
| WO | 03014398 A2 | 2/2003 |
| WO | 03027328 A2 | 4/2003 |
| WO | 03054209 A2 | 7/2003 |
| WO | 2006007841 A2 | 1/2006 |
| WO | 2006023919 A2 | 3/2006 |
| WO | 2006066039 A2 | 6/2006 |
| WO | 2006117596 A2 | 11/2006 |
| WO | 2007019492 A2 | 2/2007 |
| WO | 2007037341 A1 | 4/2007 |
| WO | 2007058326 A1 | 5/2007 |
| WO | 2007109441 A2 | 9/2007 |
| WO | 2009074154 A2 | 6/2009 |
| WO | 2009144581 A1 | 12/2009 |
| WO | 2009147537 A2 | 12/2009 |

OTHER PUBLICATIONS

U.S. Appl. No. 12/994,492, "Office Action dated May 7, 2014", 7 pages.
U.S. Appl. No. 13/203,137, "Office Action dated Jun. 10, 2014", 20 pages.
U.S. Appl. No. 13/203,149, "Office Action dated Jul. 30, 2014", 31 pages.
U.S. Appl. No. 13/513,164, "Office Action dated Aug. 22, 2014", 51 pages.
USPTO, "Notice of Allowance, Examiner-Initiated Interview Summary, and Reasons for Allowability, dated Feb. 20, 2013, in U.S. Appl. No.", 12/526,323, filed Feb. 16, 2010, 10 pages.
USPTO, "Office Action", U.S. Appl. No. 13/203,137, dated Jun. 10, 2014, 1-20.
USPTO, "Office Action dated Mar. 18, 2013", U.S. Appl. No. 13/203,149, filed Aug. 24, 2011, 16 pages.
USPTO, "Office Action dated Oct. 4, 2013", U.S. Appl. No. 13/203,149, 19 pages.
Wahl, et al., "Efficient transfer of large DNA fragments from agarose gels to diazobenzyloxymethyl-paper and rapid hybridization by using dextran sulfate", Proc. Natl. Acad. Sci. USA. Biochemisty, vol. 76, No. 8, Aug. 1979, 3683-3687.
Woenckhause, et al., "Multitarget FISH and LOH analysis at chromosome 3p in non-small cell lung cancer and adjacent bronchial epithelium", Am. J. of Clin. Pathol., vol. 123, No. 752, 2005, 10 pages.
Xi, et al., "Use of DNA and Peptide Nucleic Acid Molecular Beacons for Detection and Quantification of rRNA in Solution and in Whole Cells", Applied and Environmental Microbiology, vol. 69, No. 9, Sep. 2003, 5673-5678.
"20X SSC Recipe", Bioprotocols.info (retrieved on Jul. 28, 2014 from the internet: https://www.biogrotocols.info./reagent and buffer recipes/20x-SSC php, Jul. 28, 2014, 1 page.
"2-pyrrolidone", Wikipedia Webpage, Nov. 1, 2012, 1 page.
"DOW Ethylene Glycols", Webpage, Jun. 28, 2012, 2 pages.
"DOW Propylene Glycol", Webpage, Jun. 28, 2012, 2 pages.
"Office Action for U.S. Appl. No. 13/203,149", dated Jul. 30, 2014, 31 pages.
"Office Action for U.S. Appl. No. 12/994,492", dated May 7, 2014, 7 pages.
"Office Action for U.S. Appl. No. 12/994,495", dated Aug. 12, 2014, 20 pages.
"Office Action for U.S. Appl. No. 13/513,164", dated Aug. 22, 2014, 51 pages.
"Office Action issued in U.S. Appl. No. 13/203,137", dated Sep. 18, 2013, 33 pages.
"Optim synthetic Glycerine—Vapor Pressure and Boiling Point", Webpage, Jun. 28, 2007, 1 Page.
"Stratagene Catalogue", 1988, p. 39.
"Superscript™ First-Strand Synthesis System for RT-PCR", Invitrogen by Life Technologies, Mar. 5, 2007, 4 pages.
"TOP2A FISH pharmDxTM Kit", DAKO Catalog, May 24, 2007, 1-33.
U.S. Appl. No. 12/526,323, "Office Action in U.S. Application", dated Jul. 17, 2012, 16 pages.
U.S. Appl. No. 12/994,495, "Office Action", dated Aug. 12, 2014, 20 pages.
U.S. Appl. No. 12/994,495, "Office Action in U.S. Application", dated May 6, 2013, 17 pages.
U.S. Appl. No. 12/994,495, "Office Action in U.S. Application", dated Dec. 13, 2013, 26 pages.
U.S. Appl. No. 12/994,495, "Office Action dated Nov. 6, 2012, in U.S. Application", dated May 23, 2011, 20 pages.
Ahern, et al., "The Scientist", vol. 9, No. 20, 1995, 7 pages.
Beebe, "Glycerin Antigen Retrieval", Microscopy Today, 9:30-31, 1999, 3.
Boehringer, "Nucleic Acid Hybridization—General Aspects", Biochemicals catalog, Jan. 1, 1992, 14-17.
Brown, et al., "Analysis of RNA by Northern and Slot Blot Hybridization", Current Protocols in Molecular Biology, Unit 4.9, 2004, 19.

(56) References Cited

OTHER PUBLICATIONS

Chakrabarti, et al., "The enhancement of PCR amplification by low molecular weight amides", Nucleic Acids research, vol. 29, No. 11, 2001, 2377-2387.

Chakrabarti, et al., "The enhancement of PCR amplification by low-molecular weight sulfones", Gene, vol. 274, 2001, 293-298.

Chardonnet, et al., "Human papillomavirus detection in cervical cells by in situ hybridization with biotinylated probes", Cytopathy, vol. 3, No. 6, 1992, 341-350.

Cox, et al., "Fluorescent DNA hybridization probe preparation using amine modification and reactive dye coupling", Biotechniques, vol. 36, No. 1, Jan. 2004, 114-122.

European Patent Office, "Extended EP Search Report dated Aug. 14, 2013", application No. 13164099.7, 5 pages.

European Patent Office, "Extended European Search Report", corresponding EP Application No. 13164094.8, dated Aug. 8, 2013, 5 pages.

Hayat, "Factors Affecting Antigen Retrieval", Chapter 4 of Microscopy, Immunohistochemistry and Antigen Retrieval, New York, 2002, 71-93.

Huber, et al., "Detection of Partial Denaturation in AT-Rich DNA Fragments by /on-Pair Reserved-Phase Chromatography", Anal. Chern., vol. 68, No. 17, Sep. 1, 1996, 2959-2965.

Kiyama, et al., "In Situ Hybridization Method", New Genetic Engineering Handbook, Experimental Medical Edition, Muramatsu Masami, et al. Editors, Apr. 20, 1996, 202-203.

Kurreck, "Improvement through novel chemical modifications", Eur. J. Biochem., vol. 270, 2003, 1628-1644.

Luo et al., "Establishment of a simple and useful way for preimplantation genetic diagnosis of chromosomal diseases", Journal of Huazhong University of Science and Technology, vol. 27, No. 3, 2007, 315-317.

Lyondeii, Webpage, Mar. 7, 2013, 1 page.

Markarian, et al., "Effect of Diethylsulfoxide on the Thermal Denaturation of DNA", Department of Chemistry, Yerevan State University, Armenia, Jan. 19, 2006, 1-5.

Mochizuki, et al., "Solvent effect on PCR from a viewpoint of a change of microscopic environment of Mg(2+) in a solution", Biochem. Biophys. Res. Commun., Jun. 6, 2007, 1 page.

Moroni, et al., "Gene Copy Number for Epidermal Growth Factor Receptor (EGFR) and Clinical Response to AntiEGFR Treatment in Colorectal Cancer: A Cohort Study", Lancet Oncology, vol. 6, 2005, 279-286.

Nielsen, et al., "PNA suppression method combined with fluorescence in situ hybridization (FISH) technique", Chapter 10 of PRINS and PNA Technologies in Chromosomal Investigation (Ed. Franck Peliesitor), 2006, 22 pages.

Olsen, et al., "Amplification of HER2 and TOP2A and deletion of TOP2A genes in breast cancer investigated by new FISH probes", Acta Onco/ogia, vol. 43, No. 1, 2004, 34-42.

PCT/DK2008/000066, "International Search Report for International Application", dated Jun. 16, 2008, 3 pages.

PCT/IB2009/005893, "International Search Report and Written Opinion for International Application", dated Sep. 22, 2009, 14 pages.

PCT/IB2009/006548, "International Search Report and Written Opinion for International Application", dated Feb. 15, 2010, 14 pages.

PCT/IB2009/007725, "International Search Report and Written Opinion for International Application", dated May 7, 2010, 12 pages.

PCT/IB2009/007917, "International Search Report and Written Opinion for International Application", dated Apr. 28, 2010, 15 pages.

PCT/IB2010/000659, "International Search Report and Written Opinion issueed in International Patent Application", dated Jul. 12, 2010, 16 pages.

Powell, et al., "Metallographic in situ hybridization", Human Pathol., vol. 38, 2007, 1145-1159.

Sharpiro, et al., "Detection of N-myc gene amplification by fluorescence in situ hybridization", Am. J. Pathology, vol. 145, No. 5, 1993, 8 pages.

Stender, et al., "Fluorescence In Situ Hybridization Assay Using Peptide Nucleic Acid Probes for Differentiation between Tuberculous and Nontuberculous *Mycobacterium* Species in Smears of *Mycobacterium* Cultures", Journal of clinical microbiology, vol.. 37, No. 9, Sep. 1, 1999, 2760-2765.

Summersgill, et al., "Fluorescence and chromogenic in situ hybridization to detect genetic aberrations in formalin-fixed paraffin embedded material, including tissue microarrays", Nature Protocols, vol. 3, No. 2, Jan. 2008, 220-234.

Tkachuk, et al., "Detection of bcr-abl fusion in Chronic Myelogenous Leukemia by in situ hybridization", Science, vol. 250, No. 559, 1990, 4 pages.

Extended Search Report dated Sep. 28, 2017 for European Patent Application No. 17166012.9, filed on Feb. 26, 2010.

* cited by examiner

COMPOSITIONS AND METHODS FOR PERFORMING HYBRIDIZATIONS WITH SEPARATE DENATURATION OF THE SAMPLE AND PROBE

CROSS-REFERENCE TO RELATED APPLICATIONS

This is a continuation of U.S. application Ser. No. 13/203,160, filed Aug. 24, 2011, which is a US national stage application of International Application No. PCT/IB2010/000659, filed Feb. 26, 2010, and also claims the benefit of U.S. Provisional Patent Application No. 61/289,617, filed Dec. 23, 2009, and U.S. Provisional Patent Application No. 61/155,683, filed Feb. 26, 2009.

FIELD OF THE INVENTION

The present invention relates to compositions and methods for hybridization applications involving separate denaturation of the target and probe. In one embodiment, the present invention can be used for the in vivo, in vitro, and in situ molecular examination of DNA and RNA. In particular, the invention can be used for the molecular examination of DNA and RNA in the fields of cytology, histology, and molecular biology. In other embodiments, the present invention can be used for in situ hybridization (ISH) applications.

BACKGROUND AND DESCRIPTION

Double stranded nucleic acid molecules (i.e., DNA (deoxyribonucleic acid), DNA/RNA (ribonucleic acid) and RNA/RNA) associate in a double helical configuration. This double helix structure is stabilized by hydrogen bonding between bases on opposite strands when bases are paired in a particular way (A+T/U or G+C) and hydrophobic bonding among the stacked bases. Complementary base paring (hybridization) is central to all processes involving nucleic acid.

In a basic example of hybridization, nucleic acid probes or primers are designed to bind, or "hybridize," with a target nucleic acid, for example, DNA or RNA in a sample. One type of hybridization application, in situ hybridization (ISH), includes hybridization to a target in a specimen wherein the specimen may be in vivo, in situ, or in vitro, for example, fixed or adhered to a glass slide. The probes may be labeled to make identification of the probe-target hybrid possible by use of a fluorescence or bright field microscope/scanner.

The efficiency and accuracy of nucleic acid hybridization assays mostly depend on at least one of three major factors: a) denaturation conditions, b) renaturation conditions, and c) post-hybridization washing conditions.

In order for probes or primers to bind to a target nucleic acid in a sample, complementary strands of nucleic acid must be separated. This strand separation step, termed "denaturation," typically requires aggressive conditions to disrupt the hydrogen and hydrophobic bonds in the double helix. The probe and target molecules can either be denatured separately or together (co-denaturation). It has been argued that separate denaturation preserves morphology better, whereas co-denaturation reduces the number of practical steps. For these reasons, separate denaturation steps are most often used in molecular cytogenetics applications, and co-denaturation is most often used when tissue sections are analyzed.

Traditional hybridization experiments, such as ISH assays, use a formamide-containing solution to denature doubled stranded nucleic acid. Formamide disrupts base pairing by displacing loosely and uniformly bound hydrate molecules, and by causing "formamidation" of the Watson-Crick binding sites. Thus, formamide has a destabilizing effect on double stranded nucleic acids and analogs.

Once the complementary strands of nucleic acid have been separated, a "renaturation" or "reannealing" step allows the primers or probes to bind to the target nucleic acid in the sample. This step is also sometimes referred to as the "hybridization" step. Although formamide promotes denaturation of double stranded nucleic acids and analogs, it also significantly prolongs the renaturation time, as compared to aqueous denaturation solutions without formamide. Indeed, the re-annealing step is by far the most time-consuming aspect of traditional hybridization applications. Examples of traditional hybridization times are shown in FIGS. 1 and 2.

In addition, formamide has disadvantages beyond a long processing time. Formamide is a toxic, hazardous material, and is subject to strict regulations for use and waste. Furthermore, the use of a high concentration of formamide can cause morphological destruction of cellular, nuclear, and/or chromosomal structure, resulting in high background signals during detection.

Thus, a need exists for overcoming the drawbacks associated with prior art hybridization applications. By addressing this need, the present invention provides several potential advantages over prior art hybridization applications.

SUMMARY OF THE INVENTION

It is an object of the present invention to provide methods and compositions which result in hybridization applications having at least one of the following advantages over prior art hybridization applications: lower background, more homogenous background, preservation of sample morphology, easier automation, faster procedure, and safer (less-toxic) reagents. One way in which the present invention achieves those objectives is by providing methods and compositions for separate denaturation of the probe and the target.

The compositions and methods of the invention are applicable to any hybridization technique. The compositions and methods of the invention are also applicable to any molecular system that hybridizes or binds using base pairing, such as, for example, DNA, RNA, PNA, LNA, and synthetic and natural analogs thereof.

The nucleic acid hybridization methods and compositions of the present invention may be used for the in vivo, in vitro, or in situ analysis of genomic DNA, chromosomes, chromosome fragments, genes, and chromosome aberrations such as translocations, deletions, amplifications, insertions, mutations, or inversions associated with a normal condition or a disease. Further, the methods and compositions are useful for detection of infectious agents as well as changes in levels of expression of RNA, e.g., mRNA and its complementary DNA (cDNA).

Other uses include the in vivo, in vitro, or in situ analysis of messenger RNA (mRNA), viral RNA, viral DNA, small interfering RNA (siRNA), small nuclear RNA (snRNA), non-coding RNA (ncRNA, e.g., tRNA and rRNA), transfer messenger RNA (tmRNA), micro RNA (miRNA), piwi-interacting RNA (piRNA), long noncoding RNA, small nucleolar RNA (snoRNA), antisense RNA, double-stranded RNA (dsRNA), methylations and other base modifications, single nucleotide polymorphisms (SNPs), copy number variations (CNVs), and nucleic acids labeled with, e.g., radioisotopes, fluorescent molecules, biotin, digoxigenin (DIG), or antigens, alone or in combination with unlabeled nucleic acids.

The nucleic acid hybridization method and compositions of the present invention are useful for in vivo, in vitro, or in situ analysis of nucleic acids using techniques such as northern blot, Southern blot, flow cytometry, autoradiography, fluorescence microscopy, chemiluminescence, immunohistochemistry, virtual karyotype, gene assay, DNA microarray (e.g., array comparative genomic hybridization (array CGH)), gene expression profiling, Gene ID, Tiling array, gel electrophoresis, capillary electrophoresis, and in situ hybridizations such as FISH, SISH, CISH. The methods and compositions of the invention may be used on in vitro and in vivo samples such as bone marrow smears, blood smears, paraffin embedded tissue preparations, enzymatically dissociated tissue samples, bone marrow, amniocytes, cytospin preparations, imprints, etc.

In one embodiment, the invention provides methods and compositions for hybridizing at least one molecule (e.g., a probe) to a target (e.g., a biological sample) using separate denaturation steps for the molecule and target. In other embodiments, the invention may eliminate the use of, or reduce the dependence on formamide in such denaturation steps from, e.g., 70% formamide in traditional denaturation buffers to 50%, 25%, 15%, 10%, 5%, 2%, 1% or 0% v/v formamide in the compositions and methods of the invention. Thus, in some aspects, the present invention overcomes several disadvantages associated with traditional hybridization assays, including the major toxicity issue and the time consuming renaturation step associated with the use of formamide in such traditional hybridization assays.

One aspect of the invention is a composition or solution for separately denaturing a probe and target in hybridization applications. The composition for denaturing the target may comprise the same components as the composition for denaturing the probe, or the two compositions may comprise different components. Compositions for use in the invention may include an aqueous composition comprising at least one polar aprotic solvent in an amount effective to denature double-stranded nucleotide sequences. An amount effective to denature double-stranded nucleotide sequences is an amount that enables hybridization. For example, one way to test for whether the amount of polar aprotic solvent is effective to enable hybridization is to determine whether the polar aprotic solvent, when used in the hybridization methods and compositions described herein, such as example 1, yield a detectable signal and/or an amplified nucleic acid product.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, 50% to 60%, or 60% to 70% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

According to another aspect of the present invention the aqueous compositions comprising a polar aprotic solvent have reduced toxicity. For example, a less-toxic composition than traditional solutions used in hybridization applications may comprise a composition with the proviso that the composition does not contain formamide, or with the proviso that the composition contains less than 25%, or less than 10%, or less than 5%, or less than 2%, or less than 1%, or less than 0.5%, or less than 0.1%, or less than 0.05%, or less than 0.01% formamide. A less-toxic composition may, in one embodiment, also comprise a composition with the proviso that the composition does not contain dimethyl sulfoxide (DMSO), or with the proviso that the composition contains less than 25%, 10%, 5%, 2%, or less than 1%, or less than 0.5%, or less than 0.1%, or less than 0.05%, or less than 0.01% DMSO.

In one aspect of the invention, suitable polar aprotic solvents for use in the invention may be selected based on their Hansen Solubility Parameters. For example, suitable polar aprotic solvents may have a dispersion solubility parameter between 17.7 to 22.0 $MPa^{1/2}$, a polar solubility parameter between 13 to 23 $MPa^{1/2}$, and a hydrogen bonding solubility parameter between 3 to 13 $MPa^{1/2}$.

According to one aspect of the present invention, suitable polar aprotic solvents for use in the invention are cyclic compounds. A cyclic compound has a cyclic base structure. Examples include the cyclic compounds disclosed herein. In other embodiments, the polar aprotic solvent may be chosen from Formulas 1-4 below:

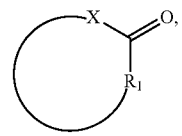

Formula 1

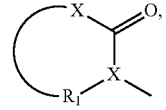

Formula 2

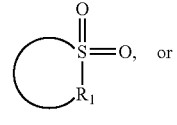

Formula 3

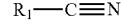

Formula 4 where X is O and R1 is alkyldiyl.

According to another aspect of the invention, suitable polar aprotic solvents for use in the invention may be chosen from Formula 5 below:

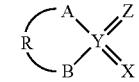

Formula 5 where X is optional and if present, is chosen from O or S;
where Z is optional and if present, is chosen from O or S;
where A and B independently are O or N or S or part of the alkyldiyl or a primary amine;
where R is alkyldiyl; and
where Y is O or S or C.

Examples of suitable polar aprotic solvents according to Formula 5 are provided in Formulas 6-9 below:

Formula 6

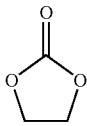

where:
X is non-existing;
A, B, and Z are O;
Y is C; and
R is Ethane-1,2 diyl;

Formula 7

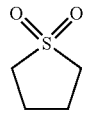

where:
Z and X are O;
A and B are part of the alkyldiyl;
Y is S; and
R is Butane-1,4 diyl;

Formula 8

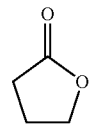

where:
X is non-existing;
A is part of the alkyldiyl;
Y is C;
B and Z is O; and
R is Propane-1,3 diyl;

Formula 9

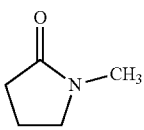

where:
X is non-existing;
A is part of the alkyldiyl;
Y is C;
B is methylamine;
Z is O; and
R is Propane-1,3 diyl According to yet another aspect of the invention the polar aprotic solvent has lactone, sulfone, nitrile, sulfite, or carbonate functionality. Such compounds are distinguished by their relatively high dielectric constants, high dipole moments, and solubility in water.

According to another aspect of the invention the polar aprotic solvent having lactone functionality is γ-butyrolactone (GBL), the polar aprotic solvent having sulfone functionality is sulfolane (SL), the polar aprotic solvent having nitrile functionality is acetonitrile (AN), the polar aprotic solvent having sulfite functionality is glycol sulfite/ethylene sulfite (GS), and the polar aprotic solvent having carbonate functionality is ethylene carbonate (EC), propylene carbonate (PC), or ethylene thiocarbonate (ETC). In yet another aspect of the invention, the compositions and methods of the invention comprise a polar aprotic solvent, with the proviso that the polar aprotic solvent is not acetonitrile (AN) or sulfolane (SL).

According to yet another aspect, the invention discloses a method of hybridizing nucleic acid sequences comprising:
combining a first nucleic acid sequence with a first aqueous composition comprising at least one polar aprotic solvent in an amount effective to denature a double-stranded nucleotide sequence,
combining a second nucleic acid sequence with a second aqueous composition comprising at least one denaturing agent in an amount effective to denature double-stranded nucleotide sequence, and
combining the first and the second nucleic acid sequences for at least a time period sufficient to hybridize the first and second nucleic acid sequences.

According to yet another aspect, the invention discloses a method of hybridizing nucleic acid sequences comprising:
combining a first nucleic acid sequence with a first aqueous composition comprising at least one polar aprotic solvent in an amount effective to denature a double-stranded nucleotide sequence, and
applying a second aqueous composition comprising a second nucleic acid sequence and at least one denaturing agent in an amount effective to denature double-stranded nucleotide sequences to said first nucleic acid sequence for at least a time period sufficient to hybridize the first and second nucleic acid sequences.

In one embodiment, the denaturing agent in the second aqueous composition is a polar aprotic solvent. In one embodiment, the first and second aqueous compositions comprise the same components. In another embodiment, the first and second aqueous compositions comprise different components.

In one embodiment, the first nucleic acid sequence is in a biological sample. In another embodiment, the biological sample is a cytology or histology sample.

In one embodiment, the first nucleic acid sequence is a single stranded sequence and the second nucleic acid sequence is a double stranded sequence. In another embodiment, the first nucleic acid sequence is a double stranded sequence and the second nucleic acid sequence is a single stranded sequence. In yet another embodiment, both the first and second nucleic acid sequences are double stranded. In yet another embodiment, both the first and second nucleic acid sequences are single stranded.

In one embodiment, a sufficient amount of time to denature the first nucleic acid sequence is provided. In one embodiment, a sufficient amount of energy to denature the first nucleic acid sequence is provided. In another embodiment, a sufficient amount of time to denature the second nucleic acid sequence is provided. In another embodiment, a sufficient amount of energy to denature the second nucleic acid sequence is provided. In another embodiment, a sufficient amount of time to hybridize the first and second nucleic acid is provided. In another embodiment, a sufficient amount of energy to hybridize the first and second nucleic acids is provided.

According to yet another aspect of the present invention, the energy is provided by heating the aqueous compositions and nucleic acid sequences. Thus, the method of the invention may include the steps of heating and cooling the aqueous compositions and nucleic acid sequences.

A further aspect of the invention comprises a method wherein the step of providing a sufficient amount of energy involves a heating step performed by the use of microwaves, hot baths, hot plates, heat wire, peltier element, induction heating, or heat lamps.

According to a further aspect, the invention relates to the use of a composition comprising between 1 and 95% (v/v)

of at least one polar aprotic solvent for the separate denaturation of a target and sample in a hybridization application.

According to yet another aspect, the invention relates to kits comprising the compositions of the invention for use in hybridization assays in which the probe and target are denatured separately.

DETAILED DESCRIPTION

A. Definitions

Figure 1:
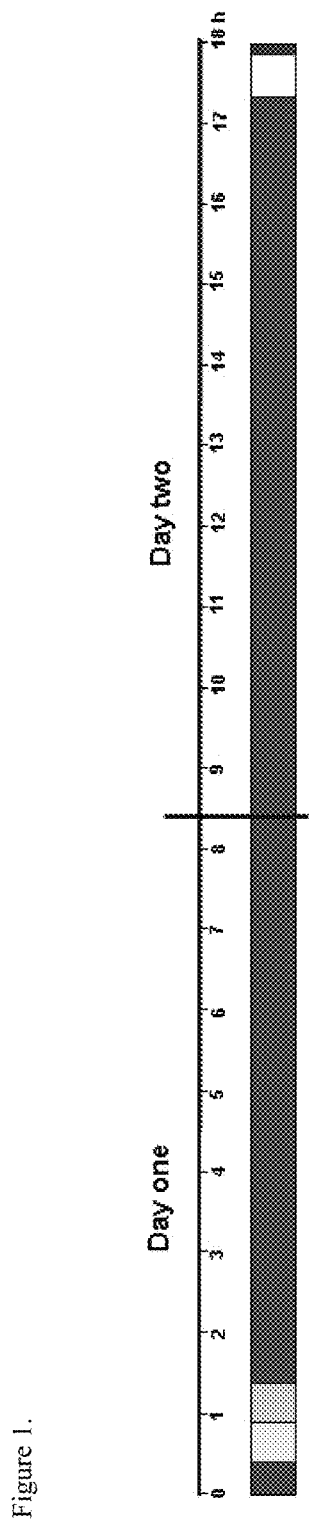
FIG. 1 depicts a typical time-course for single locus detection with primary labeled FISH probes co-denatured with formaldehyde fixed paraffin embedded tissue sections (histological specimens). The bars represent a hybridization assay performed using traditional hybridization solutions. The first bar on the left represents the deparaffination step; the second bar represents the heat-pretreatment step; the third bar represents the digestion step; the fourth bar represents the denaturation and hybridization steps; the fifth bar represents the stringency wash step; and the sixth bar represents the mounting step.
Figure 2:
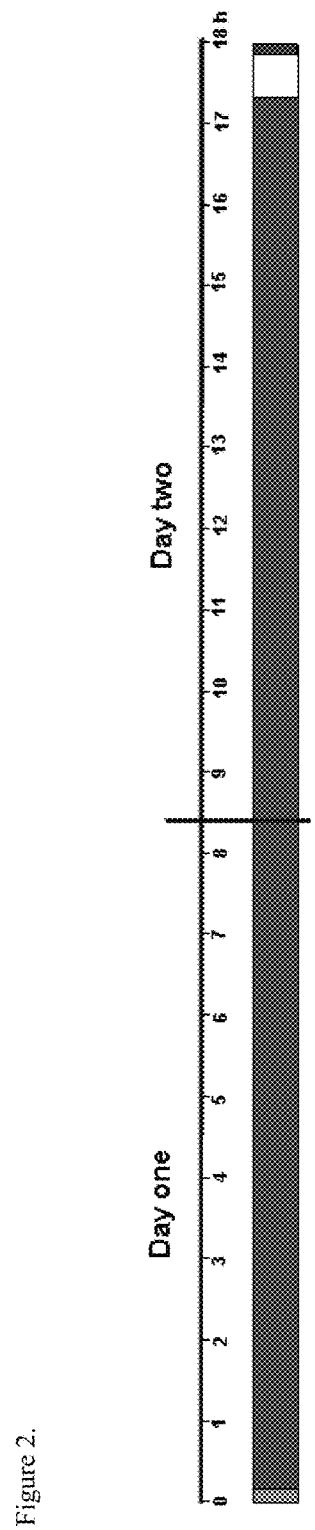
FIG. 2 depicts a typical time-course for single locus detection with primary labeled FISH probes co-denatured with cytological specimens. The bars represent a hybridization assay performed using a traditional hybridization solutions. The first bar on the left represents the fixation step; the second bar represents the denaturation and hybridization steps; the third bar represents the stringency wash step; and the fourth bar represents the mounting step.

In the context of the present invention the following terms are to be understood as follows:

"Biological sample" is to be understood as any in vivo, in vitro, or in situ sample of one or more cells or cell fragments. This can, for example, be a unicellular or multicellular organism, tissue section, cytological sample, chromosome spread, purified nucleic acid sequences, artificially made nucleic acid sequences made by, e.g., a biologic based system or by chemical synthesis, microarray, or other form of nucleic acid chip. In one embodiment, a sample is a mammalian sample, such as, e.g., a human, murine, rat, feline, or canine sample.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., a peptide nucleic acid (PNA) or locked nucleic acid (LNA)), or any derivatized form of a nucleic acid.

As used herein, the term "peptide nucleic acid" or "PNA" means a synthetic polymer having a polyamide backbone with pendant nucleobases (naturally occurring and modified), including, but not limited to, any of the oligomer or polymer segments referred to or claimed as peptide nucleic acids in, e.g., U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163, WO96/04000, all of which are herein incorporated by reference, or any of the references cited therein. The pendant nucleobase, such as, e.g., a purine or pyrimidine base on PNA may be connected to the backbone via a linker such as, e.g., one of the linkers taught in PCT/US02/30573 or any of the references cited therein. In one embodiment, the PNA has an N-(2-aminoethyl)-glycine) backbone. PNAs may be synthesized (and optionally labeled) as taught in PCT/US02/30573 or any of the references cited therein. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270:1628-44 (2003).

Examples of nucleic acids and nucleic acid analogs also include polymers of nucleotide monomers, including double and single stranded deoxyribonucleotides (DNA), ribonucleotides (RNA), α-anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof. DNA, RNA, or other nucleic acids as defined herein can be used in the method and compositions of the invention.

"Polar aprotic solvent" refers to an organic solvent having a dipole moment of about 2 debye units or more, a water solubility of at least about 5% (volume) at or near ambient temperature, i.e., about 20° C., and which does not undergo significant hydrogen exchange at approximately neutral pH, i.e., in the range of 5 to 9, or in the range 6 to 8. Polar aprotic solvents include those defined according to the Hansen Solubility Parameters discussed below.

"Alkyldiyl" refers to a saturated or unsaturated, branched, straight chain or cyclic hydrocarbon radical having two monovalent radical centers derived by the removal of one hydrogen atom from each of two different carbon atoms of a parent alkane, alkene, or alkyne.

"Aqueous solution" is to be understood as a solution containing water, even small amounts of water. For example, a solution containing 1% water is to be understood as an aqueous solution.

"Hybridization application," "hybridization assay," "hybridization experiment," "hybridization procedure," "hybridization technique," "hybridization method," etc. are to be understood as referring to any process that involves hybridization of nucleic acids. Unless otherwise specified, the terms "hybridization" and "hybridization step" are to be understood as referring to the re-annealing step of the hybridization procedure as well as the denaturation step (if present).

"Hybridization composition" refers to an aqueous solution of the invention for performing a hybridization procedure, for example, to bind a probe to a nucleic acid sequence. Hybridization compositions may comprise, e.g., at least one polar aprotic solvent, at least one nucleic acid sequence, and a hybridization solution. Hybridization compositions do not comprise enzymes or other components, such as deoxynucleoside triphosphates (dNTPs), for amplifying nucleic acids in a biological sample.

"Hybridization solution" refers to an aqueous solution for use in a hybridization composition of the invention. Hybridization solutions are discussed in detail below and may comprise, e.g., buffering agents, accelerating agents, chelating agents, salts, detergents, and blocking agents.

"Hansen Solubility Parameters" and "HSP" refer to the following cohesion energy (solubility) parameters: (1) the dispersion solubility parameter ($E_D$, "D parameter"), which measures nonpolar interactions derived from atomic forces; (2) the polar solubility parameter (bp, "P parameter"), which measures permanent dipole-permanent dipole interactions; and (3) the hydrogen bonding solubility parameter ($S_H$, "H parameter"), which measures electron exchange. The Hansen Solubility Parameters are further defined below.

"Repetitive Sequences" is to be understood as referring to the rapidly reannealing (approximately 25%) and/or intermediately reannealing (approximately 30%) components of mammalian genomes. The rapidly reannealing components contain small (a few nucleotides long) highly repetitive sequences usually found in tandem (e.g., satellite DNA), while the intermediately reannealing components contain interspersed repetitive DNA. Interspersed repeated sequences are classified as either SINEs (short interspersed repeat sequences) or LINEs (long interspersed repeated sequences), both of which are classified as retrotransposons in primates. SINEs and LINEs include, but are not limited to, Alu-repeats, Kpn-repeats, di-nucleotide repeats, tri-nucleotide repeats, tetra-nucleotide repeats, penta-nucleotide repeats and hexa-nucleotide repeats. Alu repeats make up the majority of human SINEs and are characterized by a consensus sequence of approximately 280 to 300 bp that consist of two similar sequences arranged as a head to tail dimer. In addition to SINEs and LINEs, repeat sequences also exist in chromosome telomeres at the termini of chromosomes and chromosome centromeres, which contain distinct repeat sequences that exist only in the central region of a chromosome. However, unlike SINEs and LINEs, which are dispersed randomly throughout the entire genome, telomere and centromere repeat sequences are localized within a certain region of the chromosome.

"Non-toxic" and "reduced toxicity" are defined with respect to the toxicity labeling of formamide according to "Directive 1999/45/EC of the European Parliament and of the Council of 31 May 1999 concerning the approximation of the laws, regulations and administrative provisions of the Member States relating to the classification, packaging, and labelling of dangerous preparations" (ecb.jrc.it/legislation/1999L0045EC.pdf) ("Directive"). According to the Directive, toxicity is defined using the following classification order: T+"very toxic"; T "toxic", C "corrosive", Xn "harmful", .Xi "irritant." Risk Phrases ("R phrases") describe the risks of the classified toxicity. Formamide is listed as T (toxic) and R61 (may cause harm to the unborn child). All of the following chemicals are classified as less toxic than formamide: acetonitrile (Xn, R11, R20, R21, R22, R36); sulfolane (Xn, R22); γ-butyrolactone (Xn, R22, R32); and ethylene carbonate (Xi, R36, R37, R38). At the time of filing this application, ethylene trithiocarbonate and glycol sulfite are not presently labeled.

"Denaturation" as used herein means a process in which nucleic acids or proteins reduce or lose their tertiary and/or secondary structures by application of compound(s), such as e.g. a strong acid or base, a concentrated inorganic salt, an organic solvent, and/or by external stress such as e.g. heat. This means that, when denaturation relates to nucleic acids, and when said nucleic acid is double stranded, the strands might separate partially or completely. This further means that the binding interactions of the double stranded nucleic acids are weakened sufficiently by the denaturation so that hybridization with e.g. alternative complementary strands can occur more efficiently than without denaturation.

"Denaturing agent" refers to any substance that is capable of lowering the mutual binding affinity of complementary stands of nucleic acids compared to water. Non-limiting examples of typical denaturing agents include organic solvents such as formamide, urea, DMSO, and tetraalkylammonium halides or combinations thereof. Denaturation conditions are sequence dependent and are different under different environmental parameters. The melting temperature ($T_m$) can be used to adjust denaturation conditions to decrease complementary base pairing in the presence of a denaturing agent. $T_m$ is the temperature (under defined ionic strength and pH) at which 50% of the target sequence hybridizes to a perfectly matched probe. For DNA-DNA hybrids, the $T_m$ can be approximated from the following equation:

$$T_m = 81.5° C. + 16.6(\log M) + 0.41(\% GC) - 0.61(\% \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching.

"Separate denaturation" as used herein, refers to hybridization methods in which the target nucleic acid is denatured in the absence of the probe and/or that the probe is denatured in the absence of the target nucleic acid. For example, the target may be denatured in a first solution, the probe may be denatured in a second solution, and then the denatured probe may be combined with the denatured target for a time period sufficient to hybridize the target and probe. In another example, the target may be denatured in a first solution and then combined with the probe for a time period sufficient to hybridize the target and probe. In still a further example, the probe may be denatured in a first solution and then combined with the target for a time period sufficient to hybridize the target and probe.

B. Solvent Selection

Suitable polar aprotic solvents for use in the invention may be selected based on their Hansen Solubility Parameters. Methods for experimentally determining and/or calculating HSP for a solvent are known in the art, and HSP have been reported for over 1200 chemicals.

For example, the D parameter may be calculated with reasonable accuracy based on refractive index, or may be derived from charts by comparison with known solvents of similar size, shape, and composition after establishing a critical temperature and molar volume. The P parameter may be estimated from known dipole moments (see, e.g., McClellan A. L., Tables of Experimental Dipole Moments (W.H. Freeman 1963)) using Equation 1:

$$\delta_P = 37.4(\text{Dipole Moment})/V^{1/2} \quad \text{Equation 1:}$$

where V is the molar volume. There are no equations for calculating the H parameter. Instead, the H parameter is usually determined based on group contributions.

HSP characterizations are conveniently visualized using a spherical representation, with the HSP of an experimentally-determined suitable reference solvent at the center of the sphere. The radius of the sphere (R) indicates the maximum tolerable variation from the HSP of the reference solvent that still allows for a "good" interaction to take place. Good solvents are within the sphere and bad ones are outside. The distance, $R_a$, between two solvents based on their respective HSP values can be determined using Equation 2:

$$(R_a)^2 = 4(\delta_{D1} - \delta_{D2})^2 + (\delta_{P1} - \delta_{P2})^2 (\delta_{H1} - \delta_{H2})^2 \quad \text{Equation 2:}$$

where subscript 1 indicates the reference sample, subscript 2 indicates the test chemical, and all values are in MPa$^{1/2}$. Good solubility requires that $R_a$ be less than the experimentally-determined radius of the solubility sphere $R_o$. The relative energy difference between two solvents, i.e., RED number, can be calculated by taking the ratio of $R_a$ to $R_o$, as shown in Equation 3.

$$RED = R_a/R_o \qquad \text{Equation 3:}$$

carbonate functionality are ethylene carbonate (EC), propylene carbonate (PC), or ethylene trithiocarbonate (ETC). The structures of these exemplary solvents are provided below and their Hansen Solubility Parameters, RED numbers, and molar volumes are given in Table 1.

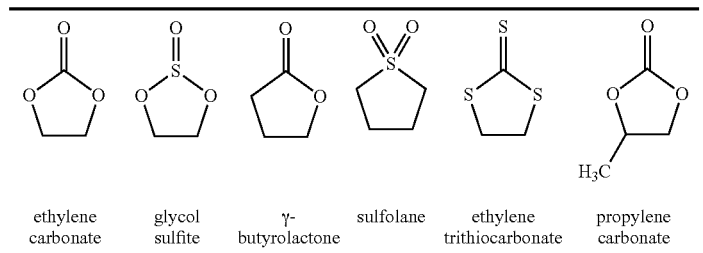

| ethylene carbonate | glycol sulfite | γ-butyrolactone | sulfolane | ethylene trithiocarbonate | propylene carbonate |

RED numbers less than 1.0 indicate high affinity; RED numbers equal or close to 1.0 indicate boundary conditions; and progressively higher RED numbers indicate progressively lower affinities.

In some embodiments, the D parameters of the polar aprotic solvents of the invention are between 17.7 to 22.0 $MPa^{1/2}$. Such relatively high D parameters are generally associated with solvents having cyclic structures and/or structures with sulfur or halogens. Linear compounds are not likely to be among the most suitable polar aprotic solvents for use in the invention, but may be considered if their P and H parameters are within the ranges discussed below. Since the D parameter is multiplied by 4 in Equation 2, the limits are one-half of $R_o$. In addition, it should be noted that D values of around 21 or higher are often characteristic of a solid.

In some embodiments, the P parameters of the polar aprotic solvents of the invention are between 13 to 23 $MPa^{1/2}$. Such exceptionally high P parameters are generally associated with solvents having a high dipole moment and presumably also a relatively low molecular volume. For example, for V near 60 cc/mole, the dipole moment should be between 4.5 and 3.1. For V near 90 cc/mole, the dipole moment should be between 5.6 and 3.9.

In some embodiments, the H parameters of the polar aprotic solvents of the invention are between 3 to 13 $MPa^{1/2}$. Generally, polar aprotic solvents having an alcohol group are not useful in the compositions and methods of the invention, since the H parameters of such solvents would be too high.

The molar volume of the polar aprotic solvent may also be relevant, since it enters into the evaluation of all three Hansen Solubility Parameters. As molar volume gets smaller, liquids tend to evaporate rapidly. As molar volume gets larger, liquids tend to enter the solid region in the range of D and P parameters recited above. Thus, the polar aprotic solvents of the invention are rather close to the liquid/solid boundary in HSP space.

In some embodiments, the polar aprotic solvents of the invention have lactone, sulfone, nitrile, sulfite, and/or carbonate functionality. Such compounds are distinguished by their relatively high dielectric constants, high dipole moments, and solubility in water. An exemplary polar aprotic solvent with lactone functionality is γ-butyrolactone (GBL), an exemplary polar aprotic solvent with sulfone functionality is sulfolane (SL; tetramethylene sulfide-dioxide), an exemplary polar aprotic solvent with nitrile functionality is acetonitrile (AN), an exemplary polar aprotic solvent with sulfite functionality is glycol sulfite/ethylene sulfite (GS), and an exemplary polar aprotic solvents with

TABLE 1

|  | D | P | H | RED | Molar Volume (cm³/mole) |
|---|---|---|---|---|---|
| Correlation ($R_0$ = 3.9) | 19.57 | 19.11 | 7.71 | — | — |
| GBL | 19.0 | 16.6 | 7.4 | 0.712 | 76.5 |
| PC | 20.0 | 18.0 | 4.1 | 0.993 | 85.2 |
| SL | 20.3 | 18.2 | 10.9 | 0.929 | 95.7 |
| EC | 19.4 | 21.7 | 5.1 | 0.946 | 66.0 |
| ETC | n/a | n/a | n/a | n/a | n/a |
| GS | 20.0 | 15.9 | 5.1 | n/a | 75.1 | n/a = not available.

Other suitable polar aprotic solvents that may be used in the invention are cyclic compounds such as, e.g., ε-caprolactone. In addition, substituted pyrolidinones and related structures with nitrogen in a 5- or 6-membered ring, and cyclic structures with two nitrile groups, or one bromine and one nitrile group, may also be suitable for use in the invention. For example, N-methyl pyrrolidinone (shown below) may be a suitable polar aprotic solvent for use in the methods and compositions of the invention.

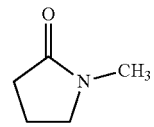

Other suitable polar aprotic solvents may contain a ring urethane group (NHCOO—). However, not all such compounds are suitable. One of skill in the art may screen for compounds useful in the compositions and methods of the invention as described herein. Exemplary chemicals that may be suitable for use in the invention are set forth in Tables 2 and 3 below.

TABLE 2

| Solvent | D | P | H |
|---|---|---|---|
| Acetanilide | 20.6 | 13.3 | 12.4 |
| N-Acetyl Pyrrolidone | 17.8 | 13.1 | 8.3 |
| 4-Amino Pyridine | 20.4 | 16.1 | 12.9 |
| Benzamide | 21.2 | 14.7 | 11.2 |
| Benzimidazole | 20.6 | 14.9 | 11.0 |
| 1,2,3-Benzotriazole | 18.7 | 15.6 | 12.4 |
| Butadienedioxide | 18.3 | 14.4 | 6.2 |

TABLE 2-continued

| Solvent | D | P | H |
|---|---|---|---|
| 2,3-Butylene Carbonate | 18.0 | 16.8 | 3.1 |
| Caprolactone (Epsilon) | 19.7 | 15.0 | 7.4 |
| Chloro Maleic Anhydride | 20.4 | 17.3 | 11.5 |
| 2-Chlorocyclohexanone | 18.5 | 13.0 | 5.1 |
| Chloronitromethane | 17.4 | 13.5 | 5.5 |
| Citraconic Anhydride | 19.2 | 17.0 | 11.2 |
| Crotonlactone | 19.0 | 19.8 | 9.6 |
| Cyclopropylnitrile | 18.6 | 16.2 | 5.7 |
| Dimethyl Sulfate | 17.7 | 17.0 | 9.7 |
| Dimethyl Sulfone | 19.0 | 19.4 | 12.3 |
| Dimethyl Sulfoxide | 18.4 | 16.4 | 10.2 |
| 1,2-Dinitrobenzene | 20.6 | 22.7 | 5.4 |
| 2,4-Dinitrotoluene | 20.0 | 13.1 | 4.9 |
| Dipheynyl Sulfone | 21.1 | 14.4 | 3.4 |
| 1,2-Dinitrobenzene | 20.6 | 22.7 | 5.4 |
| 2,4-Dinitrotoluene | 20.0 | 13.1 | 4.9 |
| Epsilon-Caprolactam | 19.4 | 13.8 | 3.9 |
| Ethanesulfonylchloride | 17.7 | 14.9 | 6.8 |
| Furfural | 18.6 | 14.9 | 5.1 |
| 2-Furonitrile | 18.4 | 15.0 | 8.2 |
| Isoxazole | 18.8 | 13.4 | 11.2 |
| Maleic Anhydride | 20.2 | 18.1 | 12.6 |
| Malononitrile | 17.7 | 18.4 | 6.7 |
| 4-Methoxy Benzonitrile | 19.4 | 16.7 | 5.4 |
| 1-Methoxy-2-Nitrobenzene | 19.6 | 16.3 | 5.5 |
| 1-Methyl Imidazole | 19.7 | 15.6 | 11.2 |
| 3-Methyl Isoxazole | 19.4 | 14.8 | 11.8 |
| N-Methyl Morpholine-N-Oxide | 19.0 | 16.1 | 10.2 |
| Methyl Phenyl Sulfone | 20.0 | 16.9 | 7.8 |
| Methyl Sulfolane | 19.4 | 17.4 | 5.3 |
| Methyl-4-Toluenesulfonate | 19.6 | 15.3 | 3.8 |
| 3-Nitroaniline | 21.2 | 18.7 | 10.3 |
| 2-Nitrothiophene | 19.7 | 16.2 | 8.2 |
| 9,10-Phenanthrenequinone | 20.3 | 17.1 | 4.8 |
| Phthalic Anhydride | 20.6 | 20.1 | 10.1 |
| 1,3-Propane Sultone | 18.4 | 16.0 | 9.0 |
| beta-Propiolactone | 19.7 | 18.2 | 10.3 |
| 2-Pyrrolidone | 19.4 | 17.4 | 11.3 |
| Saccharin | 21.0 | 13.9 | 8.8 |
| Succinonitrile | 17.9 | 16.2 | 7.9 |
| Sulfanilamide | 20.0 | 19.5 | 10.7 |
| Sulfolane | 20.3 | 18.2 | 10.9 |
| 2,2,6,6-Tetrachlorocyclohexanone | 19.5 | 14.0 | 6.3 |
| Thiazole | 20.5 | 18.8 | 10.8 |
| 3,3,3-Trichloro Propene | 17.7 | 15.5 | 3.4 |
| 1,1,2-Trichloro Propene | 17.7 | 15.7 | 3.4 |
| 1,2,3-Trichloro Propene | 17.8 | 15.7 | 3.4 |

Table 2 sets forth an exemplary list of potential chemicals for use in the compositions and methods of the invention based on their Hansen Solubility Parameters. Other compounds, may of course, also meet these requirements such as, for example, those set forth in Table 3.

TABLE 3

| Chemical (dipole moment) | RED | Melting Point ° C. |
|---|---|---|
| Chloroethylene carbonate (4.02) | 0.92 | — |
| 2-Oxazolidinone (5.07) | 0.48 | 86-89 |
| 2-Imidazole | 1.49 | 90-91 |
| 1,5-Dimethyl Tetrazole (5.3) | ~1.5 | 70-72 |
| N-Ethyl Tetrazole (5.46) | ~1.5 | — |
| Trimethylene sulfide-dioxide (4.49) | — | — |
| Trimethylene sulfite (3.63) | — | — |
| 1,3-Dimethyl-5-Tetrazole (4.02) | — | — |
| Pyridazine (3.97) | 1.16 | −8 |
| 2-Thiouracil (4.21) | — | — |
| N-Methyl Imidazole (6.2) | 1.28 | — |
| 1-Nitroso-2-pyrolidinone | ~1.37 | — |
| Ethyl Ethyl Phosphinate (3.51) | — | — |
| 5-cyano-2-Thiouracil (5.19) | — | — |
| 4H-Pyran-4-thione (4.08) | 1.35 | 32-34 |
| 4H-Pyran-4-one = gamma pyrone (4.08) | 1.49 | Boiling Point (BP) 80 |
| 2-Nitrofuran (4.41) | 1.14 | 29 |
| Methyl alpha Bromo Tetronate (6.24) | — | — |
| Tetrahydrothiapyran oxide (4.19) | 1.75 | 60-64 |
| Picolinonitrile (2-cyanopyridine) (5.23) | 0.40 | 26-28 (BP 212-215) |
| Nitrobenzimidazole (6.0) | 0.52 | 207-209 |
| Isatin (5.76) | — | 193-195 |
| N-phenyl sydnone (6.55) | — | — |
| Glycol sulfate (Ethylene glycol) | — | 99° C. |

Note:
not soluble at 40%

Some of the chemicals listed in Tables 2 and 3 have been used in hybridization and/or PCR applications in the prior art (e.g., dimethyl sulfoxide (DMSO) has been used in hybridization and PCR applications, and sulfolane (SL), acetonitrile (AN), 2-pyrrolidone, δ-caprolactam, and ethylene glycol have been used in PCR applications). Thus, in some embodiments, the polar aprotic solvent is not DMSO, sulfolane, acetonitrile, 2-pyrrolidone, ε-caprolactam, or ethylene glycol. However, most polar aprotic solvents have not been used in prior art hybridization applications. Moreover, even when such compounds were used, the prior art did not recognize that they may be advantageously used to separately denature the probe and target in such hybridization applications, as disclosed in this application.

In addition, not all of the chemicals listed in Tables 2 and 3 are suitable for use in the compositions and methods of the invention. For example, although DMSO is listed in Table 2 because its Hansen Solubility Parameters (HSPs) fall within the ranges recited above, DMSO does not function to allow separate denaturation of the probe and target in the compositions and methods of the invention. However, it is well within the skill of the ordinary artisan to screen for suitable compounds using the guidance provided herein including testing a compound in one of the examples provided. For example, in some embodiments, suitable polar aprotic solvents will have HSPs within the ranges recited above and a structure shown in Formulas 1-9 above.

C. Compositions, Buffers, and Solutions (1) Denaturation Solutions

Traditional compositions for separately or co-denaturing a probe and target in hybridization applications are known in the art. Such compositions may comprise, for example, buffering agents, accelerating agents, chelating agents, salts, detergents, and blocking agents.

For example, the buffering agents may include SSC, HEPES, SSPE, PIPES, TMAC, TRIS, SET, citric acid, a phosphate buffer, such as, e.g., potassium phosphate or sodium pyrrophosphate, etc. The buffering agents may be present at concentrations from 0.01× to 50×, such as, for example, 0.01×, 0.1×, 0.5×, 1×, 2×, 5×, 10×, 15×, 20×, 25×, 30×, 35×, 40×, 45×, or 50×. Typically, the buffering agents are present at concentrations from 0.1× to 10×.

The accelerating agents may include polymers such as FICOLL, PVP, heparin, dextran sulfate, proteins such as BSA, glycols such as ethylene glycol, glycerol, 1,3 propanediol, propylene glycol, or diethylene glycol, combinations thereof such as Dernhardt's solution and BLOTTO, and organic solvents such as formamide, dimethylformamide, DMSO, etc. The accelerating agent may be present at concentrations from 1% to 80% or 0.1× to 10×, such as, for example, 0.1% (or 0.1×), 0.2% (or 0.2×), 0.5% (or 0.5×), 1%

(or 1×), 2% (or 2×), 5% (or 5×), 10% (or 10×), 15% (or 15×), 20% (or 20×), 25% (or 25×), 30% (or 30×), 40% (or 40×), 50% (or 50×), 60% (or 60×), 70% (or 70×), or 80% (or 80×). Typically, formamide is present at concentrations from 25% to 75%, such as 25%, 30%, 40%, 50%, 60%, 70%, or 75%, while DMSO, dextran sulfate, and glycol are present at concentrations from 5% to 10%, such as 5%, 6%, 7%, 8%, 9%, or 10%.

The chelating agents may include EDTA, EGTA, etc. The chelating agents may be present at concentrations from 0.1 mM to 10 mM, such as 0.1 mM, 0.2 mM, 0.5 mM, 1 mM, 2 mM, 3 mM, 4 mM, 5 min, 6 mM, 7 mM, 8 mM, 9 mM, or 10 mM. Typically, the chelating agents are present at concentrations from 0.5 mM to 5 min, such as 0.5 mM, 1 mM, 1.5 mM, 2 mM, 2.5 mM, 3 mM, 3.5 mM, 4 mM, 4.5 mM, or 5 mM.

The salts may include sodium chloride, sodium phosphate, magnesium phosphate, etc. The salts may be present at concentrations from 1 mM to 750 mM, such as 1 mM, 5 min, 10 mM, 20 mM, 30 mM, 40 mM, 50 mM, 100 mM, 200 mM, 300 mM, 400 mM, 500 mM, 600 mM, 700 mM, or 750 mM. Typically, the salts are present at concentrations from 10 mM to 500 mM, such as 10 mM, 20 mM, 30 mM, 40 mM, 50 mM, 100 mM, 200 mM, 300 mM, 400 mM, or 500 mM.

The detergents may include Tween, SDS, Triton, CHAPS, deoxycholic acid, etc. The detergent may be present at concentrations from 0.001% to 10%, such as, for example, 0.001, 0.01, 0.1, 0.5, 1, 2, 3, 4, 5, 6, 7, 8, 9, or 10%. Typically, the detergents are present at concentrations from 0.01% to 1%, such as 0.01%, 0.02%, 0.03%, 0.05%, 0.1%, 0.2%, 0.3%, 0.4%, 0.5%, 0.6%, 0.7%, 0.8%, 0.9%, or 1%.

The nucleic acid blocking agents may include, for example, yeast tRNA, homopolymer DNA, denatured salmon sperm DNA, herring sperm DNA, total human DNA, COT1 DNA, etc. The blocking nucleic acids may be present at concentrations of 0.05 mg/mL to 100 mg/mL. However, the compositions and methods of the invention surprisingly show significantly reduced background levels without the need for blocking agents.

A great variation exists in the literature regarding traditional denaturation buffers for hybridization applications. For example, a traditional solution may comprise 5× or 6×SSC, 0.01 M EDTA, 5× Dernhardt's solution, 0.5% SDS, and 100 mg/mL sheared, denatured salmon sperm DNA. Another traditional solution may comprise 50 mM HEPES, 0.5 M NaCl, and 0.2 mM EDTA. A typical solution for FISH on biological specimens for RNA detection may comprise, e.g., 2×SSC, 10% dextran sulfate, 2 mM vanadyl-ribonucleoside complex, 50% formamide, 0.02% RNAse-free BSA, and 1 mg/mL *E. coli* tRNA. A typical solution for FISH on biological specimens for DNA detection may comprise, e.g., 2×SSC, 10% dextran sulfate, 50% formamide, and e.g., 0.3 mg/mL salmon sperm DNA or 0.1 mg/mL COT1 DNA. Other typical solutions may comprise 40% formamide, 10% dextran sulfate, 300 mM NaCl, 5 mM phosphate buffer, Alu-PNA (blocking PNA) or COT-1 DNA, and in some cases 0.1 μg/μL total human DNA (THD). Additional denaturation buffers are discussed below in the section titled "Hybridization Conditions."

The compositions of the invention may comprise any of the traditional components recited above in combination with at least one polar aprotic solvent. The traditional components may be present at the same concentrations as used in traditional denaturing solutions, or may be present at higher or lower concentrations, or may be omitted completely.

For example, if the compositions of the invention comprise salts such as NaCl and/or phosphate buffer, the salts may be present at concentrations of 0-1200 mM NaCl and/or 0-200 mM phosphate buffer. In some embodiments, the concentrations of salts may be, for example, 0 mM, 15 mM, 30 mM, 45 mM, 60 mM, 75 mM, 90 mM, 105 mM, 120 mM, 135 mM, 150 mM, 165 mM, 180 mM, 195 mM, 210 mM, 225 mM, 240 mM, 255 mM, 270 mM, 285 mM, or 300 mM NaCl and 5 mM phosphate buffer, or 600 mM NaCl and 10 mM phosphate buffer. In other embodiments, the concentrations of salts may be, for example, the concentrations present in 0.1×, 0.2×, 0.3×, 0.4×, 0.5×, 0.6×, 0.7×, 0.8×, 0.9×, 1×, 2×, 3×, 4×, 5×, 6×, 7×, or 8×SSC.

If the compositions of the invention comprise accelerating agents such as dextran sulfate, glycol, or DMSO, the dextran sulfate may be present at concentrations of from 5% to 40%, the glycol may be present at concentrations of from 0.1% to 10%, and the DMSO may be from 0.1% to 10%. In some embodiments, the concentration of dextran sulfate may be 10% or 20% and the concentration of ethylene glycol, 1,3 propanediol, or glycerol may be 1% to 10%. In some embodiments, the concentration of DMSO may be 1%. In some embodiments, the aqueous composition does not comprise DMSO as an accelerating agent. In some embodiments, the aqueous composition does not comprise formamide as an accelerating agent, or comprises formamide with the proviso that the composition contains less than 25%, or less than 10%, or less than 5%, or less than 2%, or less than 1%, or less than 0.5%, or less than 0.1%, or less than 0.05%, or less than 0.01%.

If the compositions of the invention comprise citric acid, the concentrations may range from 1 mM to 100 mM and the pH may range from 5.0 to 8.0. In some embodiments the concentration of citric acid may be 10 mM and the pH may be 6.2.

The compositions of the invention may comprise agents that reduce non-specific binding to, for example, the cell membrane, such as salmon sperm or small amounts of total human DNA or, for example, they may comprise blocking agents to block binding of, e.g., repeat sequences to the target such as larger amounts of total human DNA or repeat enriched DNA or specific blocking agents such as PNA or LNA fragments and sequences. These agents may be present at concentrations of from 0.01-100 μg/μL or 0.01-100 μM. For example, in some embodiments, these agents will be 0.1 μg/μL total human DNA, or 0.1 μg/μL non-human DNA, such as herring sperm, salmon sperm, or calf thymus DNA, or 5 μM blocking PNA. However, the compositions and methods of the invention show significantly reduced background levels without the need for blocking agents.

One aspect of the invention is a composition or solution for separately denaturing the probe and target in a hybridization application. The composition for denaturing the target may comprise the same components as the composition for denaturing the probe, or the two compositions may comprise different components. Compositions for use in the invention may include an aqueous composition comprising at least one polar aprotic solvent in an amount effective to denature double-stranded nucleotide sequences. An amount effective to denature double-stranded nucleotide sequences is an amount that enables hybridization. For example, one way to test for whether the amount of polar aprotic solvent is effective to enable hybridization is to determine whether the polar aprotic solvent, when used in the hybridization methods and compositions described herein, such as example 1, yield a detectable signal and/or an amplified nucleic acid product.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, 50% to 60%, or 60% to 70% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

If the compositions of the invention are used in a hybridization assay, they may further comprise one or more nucleic acid probes. The probes may be directly or indirectly labeled with detectable compounds such as enzymes, chromophores, fluorochromes, and haptens. The DNA probes may be present at concentrations of 0.1 to 100 ng/μL. For example, in some embodiments, the probes may be present at concentrations of 1 to 10 ng/μL. The PNA probes may be present at concentrations of 0.5 to 5000 nM. For example, in some embodiments, the probes may be present at concentrations of 5 to 1000 nM.

In one embodiment, a composition of the invention comprises a mixture of 40% polar aprotic solvent (v/v) (e.g., ethylene carbonate, "EC"), 10% dextran sulfate, 300 mM NaCl, 5 mM phosphate buffer, and 1-10 ng/μL probe. Another exemplary composition of the present invention comprises a mixture of 15% EC, 20% dextran sulfate, 600 mM NaCl, 10 mM phosphate buffer, and 0.1 μg/μl total human DNA. Yet another exemplary composition comprises 15% EC, 20% dextran sulfate, 600 mM NaCl, 10 mM citric acid pH 6.2, and 0.1 μg/μL non-human DNA (e.g., herring sperm, salmon sperm, or calf thymus) OR 0.5% formamide OR 1% glycol (e.g., ethylene glycol, 1,3 propanediol, or glycerol). Yet another exemplary composition comprises 15% EC, 20% dextran sulfate, 600 mM NaCl, 10 mM citric acid pH 6.2. Yet another exemplary composition comprises 15% EC and 10 mM citric acid pH 6.2.

(2) Polar Aprotic Solvent(s)

Different polar aprotic solvents may impart different properties on the compositions of the invention. For example, the choice of polar aprotic solvent may contribute to the stability of the composition, since certain polar aprotic solvents may degrade over time. For example, the polar aprotic solvent ethylene carbonate breaks down into ethylene glycol, which is a relatively stable molecule, and carbon dioxide, which can interact with water to form carbonic acid, altering the acidity of the compositions of the invention. Without being bound by theory, it is believed that the change in pH upon breakdown of ethylene carbonate and DNA damage from long storage makes the compositions of the invention less effective for hybridization. However, stability can be improved by reducing the pH of the composition, by adding citric acid as a buffer at pH 6.2 instead of the traditional phosphate buffer, which is typically used at about pH 7.4, and/or by adding ethylene glycol at concentrations, e.g., between 0.1% to 10%, or between 0.5% to 5%, such as, for example, 1%, 2%, 3%, etc. For example, with 10 mM citrate buffer, the compositions of the invention are stable at 2-8° C. for approximately 8 months. Stability can also be improved if the compositions are stored at low temperatures (e.g., −20° C.).

In addition, certain polar aprotic solvents may cause the compositions of the invention to separate into multi-phase systems under certain conditions. The conditions under which multi-phase systems are obtained may be different for different polar aprotic solvents. Generally, however, as the concentration of polar aprotic solvent increases, the number of phases increases. For example, compositions comprising low concentrations ethylene carbonate (i.e., less than 20%) may exist as one phase, while some compositions comprising higher concentrations of ethylene carbonate may separate into two, or even three phases. For instance, compositions comprising 15% ethylene carbonate in 20% dextran sulfate, 600 mM NaCl, and 10 mM citrate buffer exist as a single phase at room temperature, while compositions comprising 40% ethylene carbonate in 10% dextran sulfate, 300 mM NaCl, and 5 mM phosphate buffer consist of a viscous lower phase (approximately 25% of the total volume) and a less viscous upper phase (approximately 75% of the total volume) at room temperature. However, compositions comprising, e.g., 40% polar aprotic solvent (e.g., 40% EC in 10 mM citrate buffer) or 50% polar aprotic solvent (e.g., 50% EC in 2×SSC) is an one phase system.

On the other hand, some polar aprotic solvents may exist in two phases at room temperature even at low concentrations. For example, sulfolane, γ-butyrolactone, ethylene trithiocarbonate, glycol sulfite, and propylene carbonate exist as two phases at concentrations of 10, 15, 20, or 25% (20% dextran sulfate, 600 mM NaCl, 10 mM citrate buffer) at room temperature. In contrast, polar aprotic solvent compositions with lower percentages of dextran sulfate, or with no dextran sulfate, stay in one phase at room temperature (e.g. 20% GBL in 2×SSC and 20% SL in 2×SSC).

It may also be possible to alter the number of phases by adjusting the temperature of the compositions of the invention. Generally, as temperature increases, the number of phases decreases. For example, at 2-8° C., compositions comprising 40% ethylene carbonate in 10% dextran sulfate, 300 mM NaCl, and 5 mM phosphate buffer may separate into a three-phase system.

It may also be possible to alter the number of phases by adjusting the concentration of dextran sulfate and/or salt in the composition. Generally speaking, lowering the dextran sulfate concentration (traditional concentration is 10%) and/or salt concentration may reduce the number of phases. However, depending on the particular polar aprotic solvent and its concentration in the composition, single phases may be produced even with higher concentrations of salt and dextran sulfate. For example, a composition comprising low amounts of EC (e.g., 15%, 10%, or 5%) can work well by increasing the dextran sulfate and salt concentrations, while still keeping a one phase system. In a particular embodiment, compositions comprising a HER2 gene DNA probe, a CEN17 PNA probe, 15% EC, 20% dextran sulfate, 600 mM NaCl, and 10 mM phosphate buffer are frozen at −20° C. In other embodiments, the compositions are liquid at −20° C.

Some polar aprotic solvents may allow the probes to produce stronger signals in one phase or another. For example, 40% glycol sulfite produces strong signals in the lower phase and no signals in the upper phase. Similarly, certain types of probes may produce stronger signals in one phase or another. For example, PNA probes tend to show stronger signals in the lower phase than the upper phase.

Accordingly, the multiphase systems of the invention may be used to conveniently examine different aspects of a sample.

Hybridization applications may be performed with a one-phase composition of the invention, with individual phases of the multiphase compositions of the invention, or with mixtures of any one or more of the phases in a multiphase composition of the invention. For example, in a one phase system, a volume of the sample may be extracted for use in the hybridization. In a mulitphase system, one may extract a volume of sample from the phase of interest (e.g., the upper, lower, or middle phase) to use in the hybridization. Alternatively, the phases in a multiphase system may be mixed prior to extracting a volume of the mixed sample for use in the hybridization. However, the multiphase system may yield strong and uneven local background staining depending on the composition. While, the addition of low amounts of formamide will reduce background in a one phase system, it has little effect on a multiphase system with high concentrations (e.g., 40%) of a polar aprotic solvent.

Because the composition used in the hybridization step may differ from the compositions used in the separate denaturation steps, the dextran sulfate and salt concentrations of the compositions of the invention are not critical. Indeed, compositions of the invention lacking dextran sulfate, salt, and buffer produce lower background (e.g., scores that are lower by 1½ to 2) and more homogenous background in hybridization applications in which the probe and target are separately denatured, compared to hybridization applications in which the probe and target are co-denatured. However, compositions comprising a buffer (e.g., 40% EC plus 10 mM citrate buffer) produce slightly higher background (e.g., scores that are higher by ½) than unbuffered compositions. In one embodiment, compositions with EC and buffer (e.g., 15% EC plus 10 mM citrate buffer) worked without any dextran sulfate.

Hybridization applications in which the target and probe are separately denatured using the compositions of the invention produce more homogenous signal intensities and a lower more homogenous background staining than hybridization applications in which the target and probe are co-denatured using traditional buffers.

(3) Optimization for Particular Applications

The compositions of the invention can be varied in order to optimize results for a particular application. For example, the concentration of polar aprotic solvent, salt, accelerating agent, blocking agent, and/or hydrogen ions (i.e. pH) may be varied in order to improve results for a particular application.

For example, the concentration of polar aprotic solvent may be varied in order to improve signal intensity and background staining. Generally, as the concentration of polar aprotic solvent increases, signal intensity increases and background staining decreases. For example, compositions for denaturing the probe comprising 15% EC tend to show stronger signals and less background than compositions comprising 5% EC. However, signal intensity may be improved for compositions having low concentrations of polar aprotic solvent (e.g., 0% to 20%) if the concentrations of salt and/or dextran sulfate are increased. For example, strong signals may be observed with 5% to 10% EC when the salt concentration is raised approximately 3 to 4 times traditional salt concentrations (i.e., approximately 1200 mM NaCl, 20 mM phosphate buffer; traditional salt concentrations are about 300 mM NaCl). Likewise, as lower concentrations of polar aprotic solvent are used, higher concentrations of dextran sulfate are generally required to maintain good signal and background intensity.

Accordingly, the concentrations of salt and dextran sulfate may also be varied in order to improve signal intensity and background staining. Generally, as the concentrations of salt and dextran sulfate in the composition for denaturing the probe increase, the signal intensity increases and background decreases. For example, salt concentrations that are approximately two to four times traditional concentrations (i.e., 300 mM NaCl 5 mM phosphate buffer) produce strong signals and low background. Surprisingly, however, the compositions of the invention can be used even in the complete absence of salt. Signal intensities can be improved under no-salt conditions by increasing the concentrations of accelerating agent and/or polar aprotic solvent.

Likewise, compositions for denaturing the probe exhibit increased signal intensity as dextran sulfate concentration increases from 0% to 20%. However, good signals may even be observed at dextran sulfate concentrations of 0%. Signal intensity may be improved under low dextran sulfate conditions by increasing the polar aprotic solvent and/or salt concentrations.

In addition, the types probes used in the compositions of the invention may be varied to improve results. For example, in some aspects of the invention, combinations of DNA/DNA probes may show less background than combinations of DNA/PNA probes in the compositions of the invention or vice versa. On the other hand, PNA probes tend to show stronger signals than DNA probes under low salt and/or low polar aprotic solvent concentrations. In fact, PNA probes also show signals when no polar aprotic solvent is present, whereas DNA probes show weak or no signals without polar aprotic solvent.

A further optimization in the present invention is to separate the denaturation of the probe and target from each other, e.g., using a specific denaturation buffer not containing the labeled probe to denature the target. It has been found that the use of the compositions of the inventions for such separate denaturations decreases the background staining and makes the staining more homogenous both regarding the background and signal intensities. In addition, the compositions of the invention allow the separate denaturations to occur at a low temperatures, which is beneficial, for example, to preserve sample morphology and the structure of nucleic acid sequences. As discussed above, the compositions of the invention are also less toxic than, e.g., traditional formamide denaturation buffers. It is obvious for the one known in the art that such a denaturation composition for the target might consist of more traditional denaturation agent such as e.g. urea, DMSO or formamide, in place of the polar aprotic solvent, while the denaturation composition for the probe may contain a polar aprotic solvent in place of a more traditional denaturation agent. The probe and target may then be combined in the hybridizatoin step, for example, with the fast hybridization buffer described in PCT/IB09/005893.

D. Applications, Methods, and Uses (1) Analytical Samples

The methods and compositions of the invention may be used fully or partly in all types of hybridization applications comprising separate denaturation of the target and probe in the fields of cytology, histology, or molecular biology. According to one embodiment, the first or the second nucleic acid sequence in the methods of the invention is present in a biological sample. Examples of such samples include, e.g., tissue samples, cell preparations, cell fragment preparations, and isolated or enriched cell component preparations. The sample may originate from various tissues such as, e.g., breast, lung, colorectal, prostate, lung, head & neck, stomach, pancreas, esophagus, liver, and bladder, or other relevant tissues and neoplasia thereof, any cell suspension, blood sample, fine needle aspiration, ascites fluid, sputum, peritoneum wash, lung wash, urine, feces, cell scrape, cell smear, cytospin or cytoprep cells.

The sample may be isolated and processed using standard protocols. Cell fragment preparations may, e.g., be obtained by cell homogenizing, freeze-thaw treatment or cell lysing. The isolated sample may be treated in many different ways depending of the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixed followed by paraffin-embedding and cryo-preservation.

For metaphase spreads, cell cultures are generally treated with colcemid, or anther suitable spindle pole disrupting agent, to stop the cell cycle in metaphase. The cells are then fixed and spotted onto microscope slides, treated with formaldehyde, washed, and dehydrated in ethanol. Probes are then added and the samples are analyzed by any of the techniques discussed below.

Cytology involves the examination of individual cells and/or chromosome spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells are then fixed on the microscope slide before analysis by any of the techniques discussed below.

In a traditional DNA hybridization experiment using a cytological sample, slides containing the specimen are immersed in a formaldehyde buffer, washed, and then dehydrated in ethanol. The probes are then added and the specimen is covered with a coverslip. The probes and specimen are then co-denatured at a temperature sufficient to separate any double-stranded nucleic acid in the specimen (e.g. 5 minutes at 82° C.), and then incubated at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

In a traditional RNA hybridization experiment using cytological samples, cells are equilibrated in 40% formamide, 1×SSC, and 10 mM sodium phosphate for 5 min, incubated at 37° C. overnight in hybridization reactions containing 20 ng of oligonucleotide probe (e.g mix of labeled 50 bp oligos), 1×SSC, 40% formamide, 10% dextran sulfate, 0.4% BSA, 20 mM ribonucleotide vanadyl complex, salmon testes DNA (10 mg/ml), E. coli tRNA (10 mg/ml), and 10 mM sodium phosphate. Then washed twice with 4×SSC/40% formamide and again twice with 2×SSC/40% formamide, both at 37° C., and then with 2×SSC three times at room temperature. Digoxigenin-labeled probes can then e.g. be detected by using a monoclonal antibody to digoxigenin conjugated to Cy3. Biotin-labeled probes can then e.g. be detected by using streptavidin-Cy5. Detection can be by fluorescence or CISH.

Histology involves the examination of cells in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixative, and then infused with dehydrating reagent prior to analysis of the sample.

In a traditional DNA hybridization experiment using a histological sample, formalin-fixed paraffin embedded tissue specimens are cut into sections of 2-6 μm and collected on slides. The paraffin is melted (e.g., 30-60 minutes at 60° C.) and then removed (deparaffinated) by washing with xylene (or a xylene substitute), e.g., 2×5 minutes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip, the probe and specimen are co-denatured by incubating the slide at a temperature sufficient to separate any double-stranded nucleic acid (e.g. 5 minutes at 82° C.), followed by incubation at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

In a traditional RNA hybridization experiment using a histological sample, slides with FFPE tissue sections are deparaffinized in xylene for 2×5 min, immerged in 99% ethanol 2×3 min, in 96% ethanol 2×3 min, and then in pure water for 3 min. Slides are placed in a humidity chamber, Proteinase K is added, and slides are incubated at RT for 5 min-15 min. Slides are immersed in pure water for 2×3 min, immersed in 96% ethanol for 10 sec, and air-dried for 5 min. Probes are added to the tissue section and covered with coverslip. The slides are incubated at 55° C. in humidity chamber for 90 min. After incubation, the slides are immersed in a Stringent Wash solution at 55° C. for 25 min, and then immersed in TBS for 10 sec. The slides are incubated in a humidity chamber with antibody for 30 min. The slides are immersed in TBS for 2×3 min, then in pure water for 2×1 min, and then placed in a humidity chamber. The slides are then incubated with substrate for 60 min, and immersed in tap water for 5 min.

In a traditional northern blot procedure, the RNA target sample is denatured for 10 minutes at 65° C. in RNA loading buffer and immediately placed on ice. The gels are loaded and electrophoresed with 1×MOPS buffer (10×MOPS contains 200 mM morpholinopropansulfonic acid, 50 mM sodium acetate, 10 mM EDTA, pH 7.0) at 25 V overnight. The gel is then pre-equilibrated in 20×SSC for 10 min and the RNA is transferred to a nylon membrane using sterile 20×SSC as transfer buffer. The nucleic acids are then fixed on the membrane using, for example, UV-cross linking at 120 mJ or baking for 30 min at 120° C. The membrane is then washed in water and air dried. The membrane is placed in a sealable plastic bag and prehybridized without probe for 30 min at 68° C. The probe is denatured for 5 min at 100° C. and immediately placed on ice. Hybridization buffer (prewarmed to 68° C.) is added and the probe is hybridized at 68° C. overnight. The membrane is then removed from the bag and washed twice for 5 min each with shaking in a low stringency wash buffer (e.g., 2×SSC, 0.1% SDS) at room temperature. The membrane is then washed twice for 15 min each in prewarmed high stringency wash buffer (e.g., 0.1× SSC, 0.1% SDS) at 68° C. The membrane may then be stored or immediately developed for detection.

Additional examples of traditional hybridization techniques can be found, for example, in Sambrook et al., *Molecular Cloning A Laboratory Manual*, 2$^{nd}$ Ed., Cold Spring Harbor Laboratory Press, (1989) at sections 1.90-1.104, 2.108-2.117, 4.40-4.41, 7.37-7.57, 8.46-10.38, 11.7-11.8, 11.12-11.19, 11.38, and 11.45-11.57; and in Ausubel et al., *Current Protocols in Molecular Biology*, John Wiley & Sons, Inc. (1998) at sections 2.9.1-2.9.6, 2.10.4-2.10.5, 2.10.11-2.10.16, 4.6.5-4.6.9, 4.7.2-4.7.3, 4.9.7-4.9.15, 5.9.18, 6.2-6.5, 6.3, 6.4, 6.3.3-6.4.9, 5.9.12-5.9.13, 7.0.9, 8.1.3, 14.3.1-14.3.4, 14.9, 15.0.3-15.0.4, 15.1.1-15.1.8, and 20.1.24-20.1.25.

(2) Hybridization Techniques

The compositions and methods of the present invention can be used fully or partly in all types of nucleic acid hybridization techniques comprising separate denaturation of the target and probe for cytological and histological samples. Such techniques include, for example, in situ hybridization (ISH), fluorescent in situ hybridization (FISH; including multi-color FISH, Fiber-FISH, etc.), chromogenic in situ hybridization (CISH), silver in situ hybridization (SISH), comparative genome hybridization (CGH), chromosome paints, and arrays in situ.

Molecular probes that are suitable for use in the hybridizations of the invention are described, e.g., in U.S. Patent Publication No. 2005/0266459, which is incorporated herein by reference. In general, probes may be prepared by chemical synthesis, PCR, or by amplifying a specific DNA sequence by cloning, inserting the DNA into a vector, and amplifying the vector an insert in appropriate host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted and purified for use as a probe. Methods for preparing and/or synthesizing probes are known in the art, e.g., as disclosed in PCT/US02/30573.

In general, the type of probe determines the type of feature one may detect in a hybridization assay. For example, total nuclear or genomic DNA probes can be used as a species-specific probe. Chromosome paints are collections of DNA sequences derived from a single chromosome type and can identify that specific chromosome type in metaphase and interphase nuclei, count the number of a certain chromosome, show translocations, or identify extrachromosomal fragments of chromatin. Different chromosomal types also have unique repeated sequences that may be targeted for probe hybridization, to detect and count specific chromosomes. Large insert probes may be used to target unique single-copy sequences. With these large probes, the hybridization efficiency is inversely proportional to the probe size. Smaller probes can also be used to detect aberrations such as deletions, amplifications, inversions, duplications, and aneuploidy. For example, differently-colored locus-specific probes can be used to detect translocations via split-signal in situ hybridization.

In general, the ability to discriminate between closely related sequences is inversely proportional to the length of the hybridization probe because the difference in thermal stability decreases between wild type and mutant complexes as probe length increases. Probes of greater than 10 bp in length are generally required to obtain the sequence diversity necessary to correctly identify a unique organism or clinical condition of interest. On the other hand, sequence differences as subtle as a single base (point mutation) in very short oligomers (<10 base pairs) can be sufficient to enable the discrimination of the hybridization to complementary nucleic acid target sequences as compared with non-target sequences.

In one embodiment, at least one set of the in situ hybridization probes may comprise one or more PNA probes, as defined above and as described in U.S. Pat. No. 7,105,294, which is incorporated herein by reference. Methods for synthesizing PNA probes are described in PCT/US02/30573. Alternatively, or in addition, at least one set of the hybridization probes in any of the techniques discussed above may comprise one or more locked nucleic acid (LNA) probes, as described in WO 99/14226, which is incorporated herein by reference. Due to the additional bridging bond between the 2' and 4' carbons, the LNA backbone is pre-organized for hybridization. LNA/DNA and LNA/RNA interactions are stronger than the corresponding DNA/DNA and DNA/RNA interactions, as indicated by a higher melting temperature. Thus, the compositions and methods of the invention, which decrease the energy required for hybridization, are particularly useful for hybridizations with LNA probes.

In one embodiment, the probes may comprise a detectable label (a molecule that provides an analytically identifiable signal that allows the detection of the probe-target hybrid), as described in U.S. Patent Publication No. 2005/0266459, which is incorporated herein by reference. The probes may be labeled to make identification of the probe-target hybrid possible by use, for example, of a fluorescence or bright field microscope/scanner. In some embodiments, the probe may be labeled using radioactive labels such as $^{31}$P, $^{33}$P, or $^{32}$S, non-radioactive labels such as digoxigenin and biotin, or fluorescent labels. The detectable label may be directly attached to a probe, or indirectly attached to a probe, e.g., by using a linker. Any labeling method known to those in the art, including enzymatic and chemical processes, can be used for labeling probes used in the methods and compositions of the invention. In other embodiments, the probes are not labeled.

In general, in situ hybridization techniques such as CGH, FISH, CISH, and SISH, employ large, mainly unspecified, nucleic acid probes that hybridize with varying stringency to genes or gene fragments in the chromosomes of cells. Using large probes renders the in situ hybridization technique very sensitive. However, the successful use of large genomic probes in traditional hybridization assays depends on blocking the undesired background staining derived from, e.g., repetitive sequences that are present throughout the genome. Traditional methods for decreasing nonspecific probe binding include saturating the binding sites on proteins and tissue by incubating tissue with prehybridization solutions containing ficoll, bovine serum albumin (BSA), polyvinyl pyrrolidone, and nucleic acids. Such blocking steps are time-consuming and expensive. Advantageously, the methods and compositions of the invention reduce and/or eliminate the need for such blocking steps, and show significantly reduced background levels without the need for blocking agents and without the need for overnight hybridization in formamide-containing buffers. However, in one embodiment, repetitive sequences may be suppressed according to the methods known in the art, e.g., as disclosed in PCT/US02/30573.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLD-FISH). Thus, depending on the method of detection, populations of cells obtained from a sample to be tested may be visualized via fluorescence microscopy or conventional brightfield light microscopy.

Hybridization assays on cytological and histological samples are important tools for determining the number, size, and/or location of specific DNA sequences. For example, in CGH, whole genomes are stained and compared to normal reference genomes for the detection of regions with aberrant copy number. Typically, DNA from subject tissue and from normal control tissue is labeled with different colored probes. The pools of DNA are mixed and added to a metaphase spread of normal chromosomes (or to a microarray chip, for array- or matrix-CGH). The ratios of colors are then compared to identify regions with aberrant copy number.

FISH is typically used when multiple color imaging is required and/or when the protocol calls for quantification of signals. The technique generally entails preparing a cytological sample, labeling probes, denaturing target chromosomes and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. DNA sequences ranging from whole genomes down to several kilobases can be studied using FISH. With enhanced fluorescence microscope techniques, such as, for example, deconvolution, even a single mRNA molecule can be detected. FISH may also be used on metaphase spreads and interphase nuclei.

FISH has been used successfully for mapping repetitive and single-copy DNA sequences on metaphase chromosomes, interphase nuclei, chromatin fibers, and naked DNA molecules, and for chromosome identification and karyotype analysis through the localization of large repeated families, typically the ribosomal DNAs and major tandem array families. One of the most important applications for FISH has been in detecting single-copy DNA sequences, in particular disease related genes in humans and other eukaryotic model species, and the detection of infections agents. FISH may be used to detect, e.g., chromosomal aneuploidy in prenatal diagnoses, hematological cancers, and solid tumors; gene abnormalities such as oncogene amplifications, gene deletions, or gene fusions; chromosomal structural abnormalities such as translocations, duplications, insertions, or inversions; contiguous gene syndromes such as microdeletion syndrome; the genetic effects of various therapies; viral nucleic acids in somatic cells and viral integration sites in chromosomes; etc. In multi-color FISH, each chromosome is stained with a separate color, enabling one to determine the normal chromosomes from which abnormal chromosomes are derived. Such techniques include multiplex FISH (rn-FISH), spectral karyotyping (SKY), combined binary ration labeling (COBRA), color-changing karyotyping, cross-species color banding, high resolution multicolor banding, telomeric multiplex FISH (TM-FISH), split-signal FISH (ssFISH), and fusion-signal FISH.

CISH and SISH may be used for many of the same applications as FISH, and have the additional advantage of allowing for analysis of the underlying tissue morphology, for example in histopathology applications. If FISH is performed, the hybridization mixture may contain sets of distinct and balanced pairs of probes, as described in U.S. Pat. No. 6,730,474, which is incorporated herein by reference. For CISH, the hybridization mixture may contain at least one set of probes configured for detection with one or more conventional organic chromogens, and for SISH, the hybridization mixture may contain at least one set of probes configured for detection with silver particles, as described in Powell R D et al., "Metallographic in situ hybridization," Hum. Pathol., 38:1145-59 (2007).

The compositions of the invention may also be used fully or partly in all types of molecular biology techniques involving hybridization, including blotting and probing (e.g., Southern, northern, etc.), and arrays.

(3) Hybridization Conditions

The method of the present invention involves the use of polar aprotic solvents in hybridization applications comprising separate denaturation of the target and probe. The compositions of the present invention are particularly useful for separately denaturing the probe and sample in said methods.

Hybridization methods using the compositions of the invention may involve applying the compositions to a sample comprising a target nucleic acid sequence, most likely in a double stranded form. Usually, in order to secure access for the probe to hybridize with the target sequence, the probe and sample are heated together to denature any double stranded nucleic acids. It has been argued that separate denaturation preserves morphology better, whereas co-denaturation reduces the number of practical steps. For these reasons, separate denaturation steps are most often used in molecular cytogenetics applications, and co-denaturation is most often used when tissue sections are analyzed.

Denaturation typically is performed by incubating the target and probe (either together or separately) in the presence of heat (e.g., at temperatures from about 70° C. to about 95° C.) and organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03M sodium citrate). Denaturation conditions typically are established such that cell morphology is preserved (e.g., relatively low temperatures and high formamide concentrations).

In a traditional hybridization application involving separate denaturation of the target and probe, the target may be denatured, for example, at 70° C. to 85° C. for 5-30 min. in buffer comprising 50% to 70% formamide and 2×SSC, while the probe may be denatured, for example, at 75° C. to 95° C. for 5-10 minutes in 50% to 100% formamide.

Another traditional protocol for separately denaturing the probe and target may involve incubating the target at 75° C. for 2 min. in 70% (v/v) formamide, 10% (v/v) 20×SSC, and 10% (v/v) phosphate buffer, or in 70% (v/v) formamide, 2×SSC (pH7.0), and 0.1 mM EDTA, pH7.0, and incubating the probe at 75° C. for 5-10 min. in 2% (w/v) dextran sulfate, 50% formamide, 2×SSC, and 50 mM phosphate buffer. Yet another traditional protocol for separately denaturing the probe and target may involve incubating the target at room temperature for about 5 minutes in 0.05M NaOH and 2×SSC, and incubating the probe in 2×SSC, 50% formamide, 10% dextran sulfate, 0.15% SDS for 10 min. at 70–75° C.

In a traditional hybridization application involving co-denaturation of the target and probe, a typical protocol might involve incubating the target and probe together in 2×SSC, 50% formamide, 10% dextran sulfate, 0.15% SDS for 30 sec. to 5 min. at 80° C. Another traditional protocol for co-denaturing the target and probe may comprise incubating the target and probe together at 75° C. for 2-4 min. in 70% formamide and 2×SSC (adjusted to pH 7.2). Yet another traditional protocol for co-denaturing the target and probe may comprise incubating the target and probe together at 65° C. to 70° C. for 5 minutes in 50% formamide, 10% dextran sulfate, and 0.1% SDS.

In the method of the invention, however, the probe and sample are denatured in separate buffers, and then the sample and probe are combined for the hybridization step. The sample denaturation buffer and the probe denaturation buffer may comprise the same components, or may comprise different components. For example, both buffers may comprise at least one polar aprotic solvent, or only one of the two buffers may comprise a polar aprotic solvent. The polar aprotic solvent interacts with the nucleic acids and facilitates the denaturation and re-annealing steps. The polar aprotic solvent also allows for the use of lower denaturation temperatures and avoids the need for toxic chemicals, such as formamide. As a result, the polar aprotic solvents specified in the present invention produce lower background and more homogenous background, preserve sample morphology, enable easier automation, and provide safer (less-toxic) reagents.

Hybridizations using the denaturation compositions of the invention may be performed using the same assay methodology as for hybridizations performed with traditional compositions. For example, the heat pre-treatment, digestion, denaturation, hybridization, washing, and mounting steps may use the same conditions in terms of volumes, temperatures, reagents and incubation times as for traditional compositions. However, the compositions of the invention provide improved results for hybridization applications comprising separate denaturation of the probe and sample. A great variation exists in the traditional hybridization protocols known in the art. The compositions of the invention may be used in any of traditional hybridization protocols known in the art. For example, the compositions may be used in hybridization applications comprising traditional formamide hybridization buffers, or may be used in hybridization applications comprising the polar aprotic solvent hybridization buffers disclosed in PCT/IB09/005893.

Alternatively, assays using the compositions of the invention can be changed and optimized from traditional methodologies, for example, by increasing or decreasing the temperatures and/or times used to separately denature the target and probe. It will be understood by those skilled in the art that in some cases, e.g., RNA detection, denaturation steps are not required.

For example, in some embodiments, the denaturation temperatures used to separately denature the target and probe may vary from 55 to 100° C., and the hybridization temperature may vary from 20 to 55° C. In other embodiments, the denaturation temperatures may vary from 55 to 70° C., 70 to 80° C., 80 to 90° C. or 90 to 100° C., and the hybridization temperature may vary from 20 to 30° C., 30 to 40° C., 40 to 50° C., or 50 to 55° C. In other embodiments, the denaturation temperatures may be 67, 72, 82, or 92° C., and the hybridization temperature may be 37, 40, 45, or 50° C.

In other embodiments, the times for separately denaturing the sample and probe are from 0 to 15 minutes and the hybridization time may vary from 0 minutes to 72 hours. In other embodiments, the denaturation times may vary from 0 to 5 minutes, and the hybridization time may vary from 0 minute to 8 hours. In other embodiments, the denaturation times may be 0, 1, 2, 3, 4, 5, 10, 15, or 30 minutes, and the hybridization time may be 0 minutes, 5 minutes, 15 minutes, 30 minutes, 60 minutes, 180 minutes, or 240 minutes.

Accordingly, hybridizations using the compositions of the invention may be performed in less than 8 hours. In other embodiments, the hybridization step is performed in less than 6 hours. In still other embodiments, the hybridization step is performed within 4 hours. In other embodiments, the hybridization step is performed within 3 hours. In yet other embodiments, the hybridization step is performed within 2 hours. In other embodiments, the hybridization step is performed within 1 hour. In still other embodiments, the hybridization step is performed within 30 minutes. In other embodiments, they hybridization step can take place within 15 minutes. The hybridization step can even take place within 10 minutes or in less than 5 minutes.

As hybridization time changes, the concentration of probe may also be varied in order to produce strong signals and/or reduce background. For example, as hybridization time decreases, the amount of probe may be increased in order to improve signal intensity. On the other hand, as hybridization time decreases, the amount of probe may be decreased in order to improve background staining.

The compositions of the invention also eliminate the need for a blocking step during hybridization applications by improving signal and background intensity by blocking the binding of, e.g., repetitive sequences to the target DNA. Thus, there is no need to use total human DNA, blocking-PNA, COT-1 DNA, RNA, or DNA from any other source as a blocking agent. In addition, the compositions and methods of the invention surprisingly show significantly reduced background levels without the need for overnight hybridization in formamide-containing buffers.

The aqueous compositions of the invention furthermore provide for the possibility to considerably reduce the concentration of nucleic acid sequences included in the composition. Generally, the concentration of probes may be reduced from 2 to 8-fold compared to traditional concentrations. For example, if HER2 DNA probes and CEN17 PNA probes are used in the compositions of the invention, their concentrations may be reduced by ¼ and ½, respectively, compared to their concentrations in traditional hybridization compositions. This feature, along with the absence of any requirement for blocking DNA, such as blocking-PNA or COT1, allows for an increased probe volume in automated instrument systems compared to the traditional 10 μL volume used in traditional compositions systems, which reduces loss due to evaporation, as discussed in more detail below.

Reducing probe concentration also reduces background. However, reducing the probe concentration is inversely related to the hybridization time, i.e., the lower the concentration, the higher hybridization time required. Nevertheless, even when extremely low concentrations of probe are used with the aqueous compositions of the invention, the hybridization time is still shorter than with traditional compositions.

The compositions of the invention often allow for better signal-to-noise ratios than traditional hybridization compositions. For example, with certain probes, a one hour hybridization with the compositions of the invention will produce similar or lower background and stronger signals than an overnight hybridization in a traditional compositions. Background is not seen when no probe is added.

Those skilled in the art will understand that different type of hybridization assays, different types of samples, different types of probe targets, different lengths of probes, different types of probes, e.g. DNA,/RNA/PNA/LNA oligos, short DNA/RNA probes (0.5-3 kb), chromosome paint probes, CGI-1, repetitive probes (e.g. alpha-satellite repeats), single-locus etc., will effect the concentrations of, e.g., salt and polar aprotic solvents required to obtain the most effective hybridizations. The temperatures and incubation times are also important variables for hybridization applications. In view of the guidance provided herein, one skilled in the art will understand how to vary these factors to optimize the methods of the invention.

Traditional assay methods may also be changed and optimized when using the compositions of the invention depending on whether the system is manual, semi-automated, or fully automated. For example, by separating the denaturation of probe and target, it is possible to use a smaller volume of hybridization buffer in a more simple automated manner compared to co-denaturation protocols, which traditionally demand temperature ramping. Furthermore, a semi-automated or a fully automated system will benefit from the short hybridization times obtained with the compositions of the invention. The short hybridization time may reduce the difficulties encountered when traditional compositions are used in such systems. For example, one problem with semi-automated and fully automated systems is that significant evaporation of the sample can occur during hybridization, since such systems require small sample volumes (e.g., 10-150 µL), elevated temperatures, and extended hybridization times (e.g., 14 hours). Thus, proportions of the components in traditional hybridization compositions are fairly invariable. However, since the compositions of the invention allow for separate denaturation of the target and probe, evaporation is reduced, allowing for increased flexibility in the proportions of the components in hybridization compositions used in semi-automated and fully automated systems.

For example, two automated instruments have been used to perform hybridizations using the compositions of the invention in hybridization applications having a traditional co-denaturation step (i.e., the sample and probe were denatured together). Compositions comprising 40% ethylene carbonate (v/v) have been used in the apparatus disclosed in PCT application DK2008/000430, and compositions comprising 15% ethylene carbonate (v/v) have been used in the HYBRIMASTER HS-300 (Aloka CO. LTD, Japan). When the compositions of the invention are used in the HYBRIMASTER HS-300, the instrument can perform rapid FISH hybridization with water in place of the traditional toxic formamide mix, thus improving safety and reducing evaporation. If water wetted strips are attached to the lid of the inner part of the Aloka instrument's reaction unit (hybridization chamber), e.g., as described in U.S. patent application Ser. No. 11/031,514, which is incorporated herein by reference, evaporation is reduced even further. Advantageously, separate denaturation of the target and probe would decrease evaporation and sample stress in the two examples of instruments mentioned above.

Other problems with automated imaging analysis are the number of images needed, the huge amount of storage place required, and the time required to take the images. The compositions of the invention address this problem by producing very strong signals compared to traditional compositions. Because of the very strong signals produced by the compositions of the invention, the imaging can be done at lower magnification than required for traditional compositions and can still be detected and analyzed, e.g., by algorithms. Since the focal plane becomes wider with lower magnification, the compositions of the invention reduce or eliminate the requirement to take serial sections of a sample. The more homogenous background staining and signal intensities provided by the separate denaturation methods of the invention will also be beneficial for imaging analysis. As a result, the overall imaging is much faster, since the compositions of the invention require fewer or no serial sections and each image covers much greater area. In addition, the overall time for analysis is faster, since the total image files are much smaller.

Thus, the compositions and methods of the invention solve many of the problems associated with traditional hybridization compositions and methods.

The disclosure may be understood more clearly with the aid of the non-limiting examples that follow, which constitute preferred embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements. The examples that follow illustrate the present invention and should not in any way be considered as limiting the invention.

EXAMPLES

Reference will now be made in detail to specific embodiments of the invention. While the invention will be described in conjunction with these embodiments, it will be understood that they are not intended to limit the invention to those embodiments. On the contrary, the invention is intended to cover alternatives, modifications, and equivalents, which may be included within the invention as defined by the appended claims.

The reagents used in the following examples are from Dako's Histology FISH Accessory Kit (K5599) and Cytology FISH Accessory Kit (K5499) (Dako Denmark A/S, Glostrup Denmark). The kits contain all the key reagents, except for probe, required to complete a FISH procedure for formalin-fixed, paraffin-embedded tissue section specimens. All samples were prepared according to the manufacturer's description. The Dako Hybridizer (S2451, Dako) was used for the digestion, denaturation, and hybridization steps.

Evaluation of FISH slides was performed within a week after hybridization using a Leica DM6000B fluorescence microscope, equipped with DAPI, FITC, Texas Red single filters and FITC/Texas Red double filter under 10×, 20×, 40×, and 100× oil objective.

Evaluation of CISH slides was performed using an Olympus BX51 light microscope, under 4×, 10×, 20×, 40×, and 60× objective.

In the Examples that follow, "dextran sulfate" refers to the sodium salt of dextran sulfate (D8906, Sigma) having a molecular weight $M_w$>500,000. All concentrations of polar aprotic solvents are provided as v/v percentages. Phosphate buffer refers to a phosphate buffered solution containing $NaH_2PO_4$, $2H_2O$ (sodium phosphate dibasic dihydrate) and $Na_2HPO_4$, $H_2O$ (sodium phosphate monobasic monohydrate). Citrate buffer refers to a citrate buffered solution containing sodium citrate ($Na_3C_6H_5O_7$, $2H_2O$; 1.06448, Merck) and citric acid monohydrate ($C_6H_8O_7$, $H_2O$; 1.00244, Merck).

General Histology FISH/CISH Procedure for Examples 1-20

The slides with cut formalin-fixed paraffin embedded (FFPE) multiple tissue array sections from humans (tonsils, mammacarcinoma, kidney and colon) were baked at 60° C. for 30-60 min, deparaffinated in xylene baths, rehydrated in ethanol baths and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then incubated with 10 μL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity, morphology, and background of the stained slides performed the scoring.

General Cytology FISH Procedure for Examples 21-22

Slides with metaphases preparation were fixed in 3.7% formaldehyde for 2 min, washed 2×5 min, dehydrated in a series of ethanol evaporations, and air-dried. The samples were then incubated with 10 μL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity and background of the stained slides performed the scoring as described in the scoring for guidelines for tissue sections.

General Histology FISH/CISH Procedure for Examples 23-30

Slides with cut formalin-fixed paraffin embedded (FFPE) multiple tissue array sections from humans (tonsils, mammacarcinoma, kidney and colon) were baked at 60° C. for 30-60 min, deparaffinated in xylene baths, rehydrated in ethanol baths and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then either co-denatured with 10 μL FISH probe, or the FISH probe and sample were first separately denatured and then incubated together, as described under the individual experiments. The samples were then washed in Stringency Wash buffer at 65° C. 10 min, then washed 2×3 min in Wash Buffer, then dehydrated in a series of ethanol evaporations, and air-dried. Finally, the slides were mounted with 15 μl. Antifade Mounting Medium. When the staining was completed, observers trained to assess signal intensity, morphology, and background of the stained slides performed the scoring.

Scoring Guidelines of Tissue Sections

The signal intensities were evaluated on a 0-3 scale with 0 meaning no signal and 3 equating to a strong signal. The cell/tissue structures are evaluated on a 0-3 scale with 0 meaning no structure and no nuclei boundaries and 3 equating to intact structure and clear nuclei boundaries. Between 0 and 3 there are additional grades 0.5 apart from which the observer can assess signal intensity, tissue structure, and background.

The signal intensity is scored after a graded system on a 0-3 scale.

0 No signal is seen.
1 The signal intensity is weak.
2 The signal intensity is moderate.
3 The signal intensity is strong.

The scoring system allows the use of ½ grades.

The tissue and nuclear structure is scored after a graded system on a 0-3 scale.

0 The tissue structures and nuclear borders are completely destroyed.
1 The tissue structures and/or nuclear borders are poor. This grade includes situations where some areas have empty nuclei.
2 Tissue structures and/or nuclear borders are seen, but the nuclear borders are unclear. This grade includes situations where a few nuclei are empty.
3 Tissue structures and nuclear borders are intact and clear.

The scoring system allows the use of ½ grades.

The background is scored after a graded system on a 0-3 scale.

0 Little to no background is seen.
1 Some background.
2 Moderate background.
3 High Background.

The scoring system allows the use of ½ grades.

Example 1

This example compares the signal intensity and cell morphology from samples treated with the compositions of the invention or traditional hybridization solutions as a function of denaturation temperature.

FISH Probe composition I: 10% dextran sulfate, 300 mM NaCl, 5 mM phosphate buffer, 40% formamide (15515-026, Invitrogen), 5 μM blocking PNAs (see Kirsten Vang Nielsen et al., *PNA Suppression Method Combined with Fluorescence In Situ Hybridisation (FISH) Technique* inPRINS and PNA Technologies in Chromosomal Investigation, Chapter 10 (Franck Pellestor ed.) (Nova Science Publishers, Inc.

2006)), 10 ng/µL Texas Red labeled CCND1 gene DNA probe (RP11-1143E20, size 192 kb).

FISH Probe composition II: 10% dextran sulfate, 300 mM NaCl, 5 mM phosphate buffer, 40% Ethylene carbonate (03519, Fluka), 5 µM blocking PNAs, 10 ng/µL Texas Red labeled CCND1 gene DNA probe (RP11-1143E20, size 192 kb).

Phases of different viscosity, if present, were mixed before use. The FISH probes were denatured as indicated for 5 min and hybridized at 45° C. for 60 minutes.

Results:

| Denaturation temperature | Signal | | Cell morphology | |
|---|---|---|---|---|
| | (I) Formamide | (II) EC | Formamide | EC |
| 72° C. | 0 | 2 | Good | Good |
| 82° C. | ½ | 3 | Good | Good |
| 92° C. | ½ | 3 | Not good | Not good |

Signals scored as "3" were clearly visible in a 20x objective.

Example 2

This example compares the signal intensity and background staining from samples treated with the compositions of the invention or traditional hybridization solutions as a function of hybridization time.

FISH Probe composition I: 10% dextran sulfate, 300 mM NaCl, 5 mM phosphate buffer, 40% formamide, 5 µM blocking PNAs, 10 ng/µL Texas Red labeled CCND1 gene DNA probe.

FISH Probe composition II: 10% dextran sulfate, 300 mM NaCl, 5 mM phosphate buffer, 40% Ethylene carbonate, 5 µM blocking PNAs, 10 ng/µL Texas Red labeled CCND1 gene DNA probe.

Phases of different viscosity, if present, were mixed before use. The FISH probes were incubated at 82° C. for 5 min and then at 45° C. for 14 hours, 4 hours, 2 hours, 60 minutes, 30 minutes, 15 minutes, 0 minutes.

Results:

| Hybridization time | Signal | | Background staining | |
|---|---|---|---|---|
| | (I) Formamide | (II) EC | Formamide | EC |
| 14 hours | 3 | 3 | +½ | +2 |
| 4 hours | 1 | 3 | +½ | +1 |
| 2 hours | ½ | 3 | +0 | +1 |
| 60 min. | ½ | 3 | +0 | +1 |
| 30 min. | 0 | 2½ | +0 | +1 |
| 15 min. | 0 | 2 | +0 | +1 |
| 0 min. | 0 | 1 | +0 | +½ |

Signals scored as "3" were clearly visible in a 20x objective.

Example 3

This example compares the signal intensity from samples treated with the compositions of the invention having different polar aprotic solvents or traditional hybridization solutions.

FISH Probe composition I: 10% dextran sulfate, 300 mM NaCl, 5 mM phosphate buffer, 40% formamide, 5 µM blocking PNAs, 10 ng/µL Texas Red labeled CCND1 gene DNA probe.

FISH Probe composition II: 10% dextran sulfate, 300 mM NaCl, 5 mM phosphate buffer, 40% Ethylene carbonate (EC), 5 µM blocking PNAs, 10 ng/µL Texas Red labeled CCND1 gene DNA probe.

FISH Probe composition III: 10% dextran sulfate, 300 mM NaCl, 5 mM phosphate buffer, 40% Propylene carbonate (PC) (540013, Aldrich), 5 µM blocking PNAs, 10 ng/µL Texas Red labeled CCND1 gene DNA probe.

FISH Probe composition IV: 10% dextran sulfate, 300 mM NaCl, 5 mM phosphate buffer, 40% Sulfolane (SL) (T22209, Aldrich), 5 µM blocking PNAs, 10 ng/µL Texas Red labeled CCND1 gene DNA probe.

FISH Probe composition V: 10% dextran sulfate, 300 mM NaCl, 5 mM phosphate buffer, 40% Aceto nitrile (AN) (C02CIIX, Lab-Scan), 5 µM blocking PNAs, 10 ng/µL Texas Red labeled CCND1 gene DNA probe.

FISH Probe composition VI: 10% dextran sulfate, 300 mM NaCl, 5 mM phosphate buffer, 40% γ-butyrolactone (GBL) (B103608, Aldrich), 5 µM blocking PNAs, 7.5 ng/µL Texas Red labeled CCND1 gene DNA probe.

Phases of different viscosity, if present, were mixed before use. The FISH probes were incubated at 82° C. for 5 min and then at 45° C. for 60 minutes.

Results:

| Signal | | | | | |
|---|---|---|---|---|---|
| (I) Formamide | (II) EC | (III) PC | (IV) SL | (V) AN | (VI) GBL |
| ½ | 3 | 3 | 3 | 2 | 3 |

Signals scored as "3" were clearly visible in a 20x objective.

Example 4

This example compares the signal intensity from samples treated with the compositions of the invention having different concentrations of polar aprotic solvent.

FISH Probe Compositions: 10% dextran sulfate, 300 mM NaCl, 5 mM phosphate buffer, 10-60% Ethylene carbonate (as indicated), 5 µM blocking PNAs, 7.5 ng/µL Texas Red labeled IGK-constant DNA gene probe ((CTD-3050E15, RP11-1083E8; size 227 kb) and 7.5 ng/µL FITC labeled IGK-variable gene DNA probe (CTD-2575M21, RP11-122B6, RP11-316G9; size 350 and 429 kb).

Phases of different viscosity, if present, were mixed before use. The FISH probes were incubated at 82° C. for 5 min and then at 45° C. for 60 minutes.

Results:

| | | Ethylene carbonate (EC) | | | | |
|---|---|---|---|---|---|---|
| | | 10% | 20% | 30% | 40% | 60% |
| Signal intensity | Texas Red | 1½ | 2 | 3 | 3 | 2 |
| | FITC | 1 | 1½ | 2 | 2½ | 2 |

Signals scored as "3" were clearly visible in a 20x objective.

Example 5

This example compares the signal intensity and background intensity from samples treated with the compositions with and without PNA blocking.

FISH Probe Compositions: 10% dextran sulfate, 300 mM NaCl, 5 mM phosphate buffer, 40% Ethylene carbonate, 7.5 ng/μL Texas Red labeled CCND1 gene DNA probe.

Phases of different viscosity, if present, were mixed before use. The FISH probes were incubated at 82° C. for 5 min and then at 45° C. for 60 minutes.

Results:

|  | Ethylene carbonate (EC) | |
| --- | --- | --- |
|  | PNA-blocking | Non-PNA blocking |
| Signal intensity | 3 | 3 |
| Background intensity | ½+ | ½+ |

Signals scored as "3" were clearly visible in a 20x objective.

Example 6

This example compares the signal intensity from samples treated with the compositions of the invention as a function of probe concentration and hybridization time FISH Probe Compositions: 10% dextran sulfate, 300 mM NaCl, 5 mM phosphate buffer, 40% Ethylene carbonate, and 10, 7.5, 5 or 2.5 ng/μL Texas Red labeled CCND1 gene DNA probe (as indicated).

Phases of different viscosity, if present, were mixed before use. The FISH probes were incubated at 82° C. for 5 min and then at 45° C. for 3 hours, 2 hours and 1 hours.

Results:

| | Signal Intensity | | | |
| --- | --- | --- | --- | --- |
| Hybridization time | (I) 10 ng/μL | (II) 7.5 ng/μL | (III) 5 ng/μL | (IV) 2.5 ng/μL |
| 3 hours | 3 | 3 | 3 | 3 |
| 2 hours | 3 | 3 | 3 | 1 |
| 1 hours | 3 | 3 | 3 | 1/2 |

Signals scored as "3" were clearly visible in a 20x objective.

Example 7

This example compares the signal intensity from samples treated with the compositions of the invention as a function of salt, phosphate, and buffer concentrations.

FISH Probe Compositions: 10% dextran sulfate, ([NaCl], [phosphate buffer], [TRIS buffer] as indicated in Results), 40% Ethylene carbonate, 7.5 ng/μL Texas Red labeled CCND1 gene DNA probe.

Phases of different viscosity, if present, were mixed before use. The FISH probes were incubated at 82° C. for 5 min and then at 45° C. for 60 minutes.

Results:

| | [NaCl] | | |
| --- | --- | --- | --- |
| | 300 mM | 100 mM | 0 mM |
| Signal intensity phosphate [0 mM] | 2 | 1 | ½ |
| Signal intensity phosphate [5 mM] | 3 | 2½ | ½ |
| Signal intensity phosphate [35 mM] | — | — | 3 |
| Signal intensity TRIS [40 mM] | — | — | 2 |

Signals scored as "3" were clearly visible in a 20x objective.

Example 8

This example compares the signal intensity from samples treated with the compositions of the invention as a function of dextran sulfate concentration.

FISH Probe Compositions: 0, 1, 2, 5, or 10% dextran sulfate (as indicated), 300 mM NaCl, 5 mM phosphate buffer, 40% Ethylene carbonate, 5 ng/μL Texas Red labeled SIL-TAL1 gene DNA probe (RP1-278013; size 67 kb) and 6 ng/μL FITC SIL-TAL1 (ICRFc112-112C1794, RP11-184J23, RP11-8J9, CTD-2007B18, 133B9; size 560 kb).

Phases of different viscosity, if present, were mixed before use. The FISH probes were incubated at 82° C. for 5 min and then at 45° C. for 60 minutes. No blocking.

Results:

| | Signal Intensity | |
| --- | --- | --- |
| % Dextran Sulfate | Texas Red Probe | FITC Probe |
| 0% | 1 | 1 |
| 1% | 1 | 1 |
| 2% | 1½ | 1½ |
| 5% | 2 | 2½ |
| 10% | 2 | 2½ |

NOTE:
this experiment did not produce results scored as "3" because the SIL-TAL1 Texas Red labeled probe is only 67 kb and was from a non-optimized preparation.

Example 9

This example compares the signal intensity from samples treated with the compositions of the invention as a function of dextran sulfate, salt, phosphate, and polar aprotic solvent concentrations.

FISH Probe Composition Ia: 34% dextran sulfate, 0 mM NaCl, 0 mM phosphate buffer, 0% ethylene carbonate, 10 ng/μL Texas Red labeled HER2 gene DNA probe (size 218 kb) and 50 nM of FITC-labeled CEN-7 PNA probe.

FISH Probe Composition Ib: 34% dextran sulfate, 300 mM NaCl, 5 mM phosphate buffer, 0% ethylene carbonate, 10 ng/μL Texas Red labeled HER2 gene DNA probe (size 218 kb) and 50 nM of FITC-labeled CEN-7 PNA probe.

FISH Probe Composition Ic: 34% dextran sulfate, 600 mM NaCl, 10 mM phosphate buffer, 0% ethylene carbonate, 10 Texas Red labeled HER2 gene DNA probe (size 218 kb) and 50 nM of FITC-labeled CEN-7 PNA probe.

FISH Probe Composition IIa: 32% dextran sulfate, 0 mM NaCl, 0 mM phosphate buffer, 5% ethylene carbonate, 10 ng/μL Texas Red labeled HER2 gene DNA probe (size 218 kb) and 50 nM of FITC-labeled CEN-7 PNA probe.

FISH Probe Composition IIb: 32% dextran sulfate, 300 mM NaCl, 5 mM phosphate buffer, 5% ethylene carbonate, 10 ng/μL Texas Red labeled HER2 gene DNA probe (size 218 kb) and 50 nM of FITC-labeled CEN-7 PNA probe.

FISH Probe Composition IIc: 32% dextran sulfate, 600 mM NaCl, 10 mM phosphate buffer, 5% ethylene carbonate, 10 ng/μL Texas Red labeled HER2 gene DNA probe (size 218 kb) and 50 nM of FITC-labeled CEN-7 PNA probe.

FISH Probe Composition IIIa: 30% dextran sulfate, 0 mM NaCl, 0 mM phosphate buffer, 10% ethylene carbonate, 10 ng/μL Texas Red labeled HER2 gene DNA probe (size 218 kb) and 50 nM of FITC-labeled CEN-7 PNA probe.

FISH Probe Composition IIIb: 30% dextran sulfate, 300 mM NaCl, 5 mM phosphate buffer, 10% ethylene carbonate, 10 ng/μL Texas Red labeled HER2 gene DNA probe (size 218 kb) and 50 nM of FITC-labeled CEN-7 PNA probe.

FISH Probe Composition Inc: 30% dextran sulfate, 600 mM NaCl, 10 mM phosphate buffer, 10% ethylene carbonate, 10 ng/μL, Texas Red labeled HER2 gene DNA probe (size 218 kb) and 50 nM of FITC-labeled CEN-7 PNA probe.

FISH Probe Composition IVa: 28% dextran sulfate, 0 mM NaCl, 0 mM phosphate buffer, 15% ethylene carbonate, 10 ng/μL Texas Red labeled HER2 gene DNA probe (size 218 kb) and 50 nM of FITC-labeled CEN-7 PNA probe.

FISH Probe Composition IVb: 28% dextran sulfate, 300 mM NaCl, 5 mM phosphate buffer, 15% ethylene carbonate, 10 ng/μL Texas Red labeled HER2 gene DNA probe (size 218 kb) and 50 nM of FITC-labeled CEN-7 PNA probe.

FISH Probe Composition IVc: 28% dextran sulfate, 600 mM NaCl, 10 mM phosphate buffer, 15% ethylene carbonate, 10 ng/μL Texas Red labeled HER2 gene DNA probe (size 218 kb) and 50 nM of FITC-labeled CEN-7 PNA probe.

FISH Probe Reference V: Standard sales vial of HER2 PharmDx probe mix (K5331, Dako) containing blocking PNA. Overnight hybridization for 20 hours.

All compositions were present as a single phase. The FISH probes were incubated at 82° C. for 5 min and then at 45° C. for 60 minutes with no blocking, except for FISH Probe Reference V, which had PNA blocking and was hybridized for 20 hours.

Results:

|  | Signal Strength | |
|---|---|---|
|  | DNA Probes | PNA Probes |
| Composition Ia | 0 | ½ |
| Composition Ib | 0 | ½ |
| Composition Ic | ½ | 2½ |
| Composition IIa | ½ | 3 |
| Composition IIb | 1 | 2 |
| Composition IIc | ½ | 3 |
| Composition IIIa | 1 | 2½ |
| Composition IIIb | 1½ | 2½ |
| Composition IIIc | 2 | 3 |
| Composition IVa | 2½-3 | 3 |
| Composition IVb | 3 | 3 |
| Composition IVc | 3 | 3 |
| Reference V | 2 | 2½ |

NOTE:
Composition IVa gave strong DNA signals with no salt. This is not possible with standard FISH compositions, where DNA binding is salt dependent.

Example 10

This example compares the signal intensity from samples treated with the compositions of the invention as a function of polar aprotic solvent and dextran sulfate concentration under high salt (4× normal) conditions.

FISH Probe Composition I: 0% ethylene carbonate, 29% dextran sulfate, 1200 mM NaCl, 20 mM phosphate buffer, 10 ng/μL Texas Red labeled HER2 gene DNA probe and 50 nM of FITC-labeled CEN-7 PNA probe. Composition was a single phase.

FISH Probe Composition II: 5% ethylene carbonate, 27% dextran sulfate, 1200 mM NaCl, 20 mM phosphate buffer, 10 ng/μL Texas Red labeled HER2 gene DNA probe and 50 nM of FITC-labeled CEN-7 PNA probe. Composition was a single phase.

FISH Probe Composition III: 10% ethylene carbonate, 25% dextran sulfate, 1200 mM NaCl, 20 mM phosphate buffer, 10 ng/μL Texas Red labeled HER2 gene DNA probe and 50 nM of FITC-labeled CEN-7 PNA probe. Composition was a single phase.

FISH Probe Composition IV (not tested): 20% ethylene carbonate, 21% dextran sulfate, 1200 mM NaCl, 20 mM phosphate buffer, 10 ng/μL Texas Red labeled HER2 gene DNA probe and 50 nM of FITC-labeled CEN-7 PNA probe. Composition had two phases.

Results:

|  | Signal Strength | |
|---|---|---|
|  | DNA Probes | PNA Probes |
| Composition I | ½ | 3 |
| Composition II | 2 | 2½ |
| Composition III | 3 | 3 |
| Composition IV | — | — |

Note:
Composition II gave good DNA signals with only 5% EC and strong DNA signals with 10% EC.

Example 11

This example compares the signal intensity and background from samples treated with different phases of the compositions of the invention.

FISH Probe Composition: 10% dextran sulfate, 300 mM NaCl, 5 mM phosphate buffer, 40% Ethylene carbonate, 8 ng/μL Texas Red labeled HER2 gene DNA probe and 600 nM FITC-labeled CEN-17 PNA probe. The FISH probes were incubated at 82° C. for 5 min and then at 45° C. for 60 minutes. No blocking.

Results:

|  | Signal Intensity | | |
|---|---|---|---|
|  | DNA Probe | PNA Probe | Background |
| Upper Phase | 3 | 1½ | +2 |
| Lower Phase | 3 | 2½ | +1 |
| Mix of Upper and Lower Phases | 2½ | 3 | +½ |

NOTE:
the upper phase had more background than the lower phase in these experiments.

Example 12

This example is similar to the previous example, but uses a different DNA probe and GBL instead of EC.

FISH Probe Composition: 10% dextran sulfate, 300 mM NaCl, 5 mM phosphate buffer, 40% GBL, 10 ng/μL Texas Red labeled CCND1 gene DNA probe and 600 nM FITC-labeled CEN-17 PNA probe.

The FISH probes were incubated at 82° C. for 5 min and then at 45° C. for 60 minutes. No blocking.

Results:

|  | Signal Strength | | |
|---|---|---|---|
|  | DNA Probe | PNA Probe | Background |
| Top Phase | 3 | 0-½ | +1½ |
| Bottom Phase | 2 | ½ | +3 |
| Mixed Phases | 2½ | ½ | +2½ |

Example 13

This example examines the number of phases in the compositions of the invention as a function of polar aprotic solvent and dextran sulfate concentration.

FISH Probe Compositions: 10 or 20% dextran sulfate; 300 mM NaCl; 5 mM phosphate buffer; 0, 5, 10, 15, 20, 25, 30% EC; 10 ng/μL probe.

Results:

| % EC | Number of Phases 10% Dextran | Number of Phases 20% Dextran |
|---|---|---|
| 0 | 1 | 1 |
| 5 | 1 | 1 |
| 10 | 1 | 1 |
| 15 | 1 | 1 |
| 20 | 2 | 2 |
| 25 | 2 | 2 |
| 30 | 2 | 2 |

NOTE:
15% EC, 20% dextran sulfate produces the nicest high signal intensities of the above one phase solution. Two phases 20% EC has even higher signal intensities than 15%. (Data not shown).

Example 14

This example compares the signal intensity and background from samples treated with different compositions of the invention as a function of probe concentration and hybridization time.

FISH Probe Composition I: 10 ng/μL HER2 TxRed labeled DNA probe (standard concentration) and standard concentration of CEN7 FITC labeled PNA probe (50 nM); 15% EC; 20% dextran sulfate; 600 mM NaCl; 10 mM phosphate buffer.

FISH Probe Composition II: 5 ng/μL HER2 TxRed labeled DNA probe (½ of standard concentration) and standard concentration (50 nM) of FITC labeled CEN7 PNA probes; 15% EC; 20% dextran sulfate; 600 mM NaCl; 10 mM phosphate buffer.

FISH Probe Composition III: 2.5 ng/μL HER2 TxRed labeled DNA probe (¼ of standard concentration) and ½ of the standard concentration (25 nM) of CEN7 PNA probes; 15% EC; 20% dextran sulfate; 600 mM NaCl; 10 mM phosphate buffer.

Compositions I-III existed as a single phase. The FISH probes were incubated at 82° C. for 5 min and then at 45° C. for 3 hours, 2 hours and 1 hours.

Results:

| Hybridization time | Signal Intensity | | | | | | | | |
|---|---|---|---|---|---|---|---|---|---|
| | I | | | II | | | III | | |
| | DNA | PNA | B.G. | DNA | PNA | B.G. | DNA | PNA | B.G. |
| 3 hours | 3 | 3 | +3 | 3 | 3 | +2.5 | 3 | 3 | +1.5 |
| 2 hours | 2.5 | 2.5 | +3 | 3 | 3 | +3 | 3 | 3 | +1.5 |
| 1 hours | 2.5 | 2.5 | +3 | 3 | 3 | +1.5 | 2.5 | 3 | +1 |

Signals scored as "3" were clearly visible in a 20x objective.
B.G.: Back ground.

Example 15

This example compares the signal intensity and background from samples treated with the compositions of the invention as a function of blocking agent.

FISH Probe Compositions: 15% EC; 20% dextran sulfate; 600 mM NaCl; 10 mM phosphate buffer; 2.5 ng/μL HER2 TxRed labeled DNA probe (¼ of standard concentration) and ½ of the standard concentration (300 nM) FITC labeled CEN17 PNA probe. Samples were blocked with: (a) nothing; (b) 0.1 μg/μL COT1 (15279-011, Invitrogen); (c) 0.3 μg/μL COT1; or (d) 0.1 μg/μL total human DNA before hybridization using the compositions of the invention.

All samples were present as a single phase. The FISH probes were incubated at 82° C. for 5 min and then at 45° C. for 60 minutes.

Results:

| Blocking Agent | Background | Signal Intensity | |
|---|---|---|---|
| | | DNA | PNA |
| Nothing | +1-1.5 | 3 | 2.5 |
| 0.1 μg/μL COT1 | +1 | 3 | 2.5 |
| 0.3 μg/μL COT1 | +1.5 | 3 | 2.5 |
| 0.1 μg/μL total human DNA | +½ | 3 | 2.5 |

NOTE:
Background levels without blocking are significantly lower than what is normally observed by standard FISH with no blocking. In contrast, if a standard FISH composition does not contain a blocking agent, signals normally cannot be read.

Example 16

This experiment compares different ways of removing background staining using the compositions of the invention.

All compositions contained 15% EC, 20% dextran sulfate, 600 mM NaCl, 10 mM phosphate buffer, 2.5 ng/μL HER2 DNA probes (¼ of standard concentration), 300 nM CEN17 PNA probe (½ of standard concentration), and one of the following background-reducing agents:

A) 5 μM blocking-PNA (see Kirsten Vang Nielsen et al., *PNA Suppression Method Combined with Fluorescence In Situ Hybridisation (FISH) Technique* inPRINS and PNA Technologies in Chromosomal Investigation, Chapter 10 (Franck Pellestor ed.) (Nova Science Publishers, Inc. 2006))

B) 0.1 μg/μL COT-1 DNA

C) 0.1 total human DNA (THD) (sonicated unlabelled THD)

D) 0.1 μg/μL sheared salmon sperm DNA (AM9680, Ambion)

E) 0.1 μg/μL calf thymus DNA (D8661, Sigma)

F) 0.1 μg/μL herring sperm DNA (D7290, Sigma)

G) 0.5% formamide

H) 2% formamide

I) 1% ethylene glycol (1.09621, Merck)

J) 1% glycerol (1.04095, Merck)

K) 1% 1,3-Propanediol (533734, Aldrich)

L) 1% H$_2$O (control)

All samples were present as a single phase. The probes were incubated at 82° C. for 5 minutes and then at 45° C. on FFPE tissue sections for 60 and 120 minutes.

Results:

|  |  |  | Signal Intensity | |
|---|---|---|---|---|
| Background blocking | Hybridization/min | Background | DNA | PNA |
| Blocking-PNA | 60 | +1 | 3 | 2.5 |
| Blocking-PNA | 120 | +1-1½ | 3 | 2.5 |
| COT-1 | 60 | +½ | 3 | 2.5 |
| COT-1 | 120 | +0-½ | 3 | 2.5 |
| THD | 60 | +0 | 3 | 3 |
| THD | 120 | +½ | 3 | 2.5 |
| Salmon DNA sperm | 60 | +0 | 3 | 3 |
| Salmon DNA sperm | 120 | +0 | 3 | 3 |
| Calf Thymus DNA | 60 | +0 | 2.5 | 3 |
| Calf Thymus DNA | 120 | +½ | 3 | 2.5 |
| Hearing sperm DNA | 60 | +0 | 3 | 3 |
| Hearing sperm DNA | 120 | +½ | 2.5 | 3 |
| 0.5% formamide | 60 | +0 | 2.5 | 3 |
| 0.5% formamide | 120 | +0 | 3 | 3 |
| 2% formamide | 60 | +½ | 2.5 | 3 |
| 2% formamide | 120 | +½ | 3 | 3 |
| 1% Ethylene Glycol | 60 | +½ | 2.5 | 3 |
| 1% Ethylene Glycol | 120 | +1½ | 3 | 2.5 |
| 1% Glycerol | 60 | +½ | 0.5 | 3 |
| 1% Glycerol | 120 | +1 | 3 | 2.5 |
| 1% 1,3-Propanediol | 60 | +0 | 3 | 2.5 |
| 1% 1,3-Propanediol | 120 | +1 | 3 | 2.5 |
| Nothing | 60 | +1 | 2.5 | 2.5 |
| Nothing | 120 | +1½ | 3 | 2.5 |

NOTE:
all background reducing reagents, except for blocking-PNA, showed an effect in background reduction. Thus, specific blocking against repetitive DNA sequences is not required.

Example 17

This experiment compares the signal intensity from the upper and lower phases using two different polar aprotic solvents.

FISH Probe Composition I: 10% dextran sulfate, 300 mM NaCl, 5 mM phosphate buffer, 40% ethylene trithiocarbonate (ET) (E27750, Aldrich), 5 µM blocking PNAs, 10 ng/µL Texas Red labeled CCND1 gene DNA probe.

FISH Probe Composition II: 10% dextran sulfate, 300 mM NaCl, 5 mM phosphate buffer, 40% glycol sulfite (GS) (G7208, Aldrich), 5 µM blocking PNAs, 10 ng/µL Texas Red labeled CCND1 gene DNA probe.

The FISH probes were incubated at 82° C. for 5 min and then at 45° C. for 60 minutes.

Results:

|  | Signal Intensity | |
|---|---|---|
|  | I (ET) | II (GS) |
| Upper Phase | 1½ | 0 |
| Lower Phase | 0 | 3 |
| Mix of Upper and Lower Phases | 2½ | 3 |

Example 18

This experiment examines the ability of various polar aprotic solvents to form a one-phase system.

All compositions contained: 20% dextran sulfate, 600 mM NaCl, 10 mM phosphate buffer, and either 10, 15, 20, or 25% of one of the following polar aprotic solvents:

Sulfolane
γ-Butyrolactone
Ethylene trithiocarbonate
Glycol sulfite
Propylene carbonate Results: all of the polar aprotic solvents at all of the concentrations examined produced at least a two-phase system in the compositions used. However, this does not exclude that these compounds can produce a one-phase system under other composition conditions.

Example 19

This experiment examines the use of the compositions of the invention in chromogenic in situ hybridization (CISH) analysis on multi FFPE tissue sections.

FISH Probe Composition I: 4.5 ng/µL TCRAD FITC labelled gene DNA probe (¼ of standard concentration) (RP11-654A2, RP11-246A2, CTP-2355L21, RP11-158G6, RP11-780M2, RP11-481C14; size 1018 kb); 15% EC; 20% dextran sulfate; 600 mM NaCl; 10 mM citrate buffer, pH 6.0.

FISH Probe Composition II: 4.5 ng/µL TCRAD FITC labelled gene DNA probe (¼ of standard concentration) (size 1018 kb); 15% EC; 20% dextran sulfate; 600 mM NaCl; 10 mM citrate buffer, pH 6.0; 0.1 ug/uL sheared salmon DNA sperm.

FISH Probe Composition III: 300 nM of each individual FITC labelled PNA CEN17 probe (½ of standard concentration); 15% EC; 20% dextran sulfate; 600 mM NaCl; 10 mM citrate buffer, pH 6.0.

All samples were analyzed using the Dako DuoCISH protocol (SK108) and compositions for split probes with the exception that the stringency wash was conducted for 20 minutes instead of 10 minutes, and without using the DuoCISH red chromogen step.

Results:

|  | Signal Strength | |
|---|---|---|
| Composition | FITC DNA | FITC PNA |
| I | 3 | — |
| II | 3 | — |
| III | — | 3 |

Note:
The signal intensities were very strong. Due to the high levels of background, it was not possible to discriminate if addition of salmon sperm DNA in Composition II reduced the background. Signals were clearly visible using a 10x objective in e.g. tonsils, which in general had less background. If tissues possessed high background, the signals were clearly visible using a 20x objective.

Example 20

This example compares the signal intensity and background from FFPE tissue sections treated with the compositions of the invention with two DNA probes.

FISH Probe Composition I: 9 ng/µl IGH FITC labelled gene DNA probe (RP11-151B17, RP11-112H5, RP11-101G24, RP11-12F16, RP11-47P23, CTP-3087C18; size 612 kb); 6.4 ng/µL MYC Tx Red labeled DNA probe (CTD-2106F24, CTD-2151C21, CTD-2267H22; size 418 kb); 15% EC; 20% dextran sulfate; 600 mM NaCl; 10 mM citrate buffer, pH 6.0.

FISH Probe Composition II: 9 ng/µL IGH FITC labelled gene DNA probe; 6.4 ng MYC TxRed labeled DNA probe; 15% EC, 20% dextran sulfate; 600 mM NaCl; 10 mM citrate buffer, pH 6.0; 0.1 ug/uL sheared salmon sperm DNA.

| Signal Strength | | | |
|---|---|---|---|
| Salmon DNA | FITC probe | Texas Red probe | Background |
| − | 2½ | 2½ | +2.5 |
| + | 3 | 3 | +1.5 |

NOTE:
the high background was probably due to the fact that standard probe concentrations were used.

Example 21

This experiment examines the use of the compositions of the invention on cytological samples.

FISH Probe Composition: 15% EC; 20% dextran sulfate; 600 mM NaCl; 10 mM phosphate buffer; 5 ng/µL HER2 TxRed labeled DNA probe (½ of standard concentration) and ½ of the standard concentration of CENT (25 nM).

The FISH probes were incubated on metaphase chromosome spreads at 82° C. for 5 minutes, then at 45° C. for 30 minutes, all without blocking.

Results:

| Signal Strength | | |
|---|---|---|
| DNA Probe | PNA Probe | Background |
| 3 | 3 | +1 |

No chromosome banding (R-banding pattern) was observed with the compositions of the invention, in contrast with traditional ISH solutions, which typically show R-banding. A low homogenously red background staining of the interphase nuclei and metaphase chromosomes was observed.

Example 22

This example compares the signal intensity and background from DNA probes on cytology samples, metaphase spreads, with and without blocking.

FISH Probe Composition I: 6 ng/µL TCRAD Texas Red labelled gene DNA probe (standard concentration) (CTP-31666K20, CTP-2373N7; size 301 kb) and 4.5 ng/µL FITC labelled gene DNA probe (¼ of standard concentration); 15% EC, 20% dextran sulfate; 600 mM NaCl; 10 mM citrate buffer, pH 6.0.

FISH Probe Composition II: 6 ng/µL TCRAD Texas Red labelled gene DNA probe (standard concentration) (size 301 kb) and 4.5 ng/µL FITC labelled gene DNA probe (¼ of standard concentration); 15% EC, 20% dextran sulfate; 600 mM NaCl; 10 mM citrate buffer, pH 6.0; 0.1 ug/uL sheared salmon sperm DNA.

The FISH probes were incubated on metaphase spreads at 82° C. for 5 min, then at 45° C. for 60 mM.

Results:

| | | Signal Intensity | |
|---|---|---|---|
| Blocking Agent | Background | Tx Red | FITC |
| Nothing | +0 | 3 | 3 |
| 0.1 µg/µL Salmon DNA | +0 | 3 | 3 |

Again, no chromosome banding (R-banding pattern) was observed with the compositions of the invention. In addition, no background staining of the interphase nuclei or the metaphase chromosomes were observed.

Example 23

This example compares signal intensity and background for experiments involving co-denaturation of the probe and specimen before hybridization, and experiments involving separate denaturation of the probe and specimen before hybridization.

FISH Probe Composition: 2.5 ng/µL HER2 TxRed labeled DNA probe (¼ of standard concentration) and ½ of the standard concentration (300 nM) of CEN17 PNA probes; 15% EC, 20% dextran sulfate; 600 mM NaCl; 10 mM citrate buffer, pH 6.0.

Specimen denaturation composition: 15% EC, 20% dextran sulfate; 600 mM NaCl; 10 mM citrate buffer, pH 6.0.

Denaturation was performed as indicated in the table for 5 mM. Hybridization was performed at 45° C. for 60 mM. In the reference sample, the FISH probe and tissue were denatured together.

Results:

| Denaturation Temperature | Denaturation Temperature | | Signal Intensity | |
|---|---|---|---|---|
| Tissue | FISH probe | Background | DNA | PNA |
| 82° C. (reference) | | +2 | 2½ | 2½ |
| 72° C. | 72° C. | +0 | 3 | 3 |
| 82° C. | 82° C. | +1 | 3 | 3 |

These results show that background staining was lower when denaturation was performed separately on the specimen and probe. The background staining also was much more homogenous for the separate denaturation samples (data not shown).

Example 24

This example compares signal intensity and background for experiments involving co-denaturation of the probe and specimen before hybridization, and experiments involving separate denaturation of the probe and specimen before hybridization.

Specimen denaturation composition I: 15% EC, 10 mM citrate buffer, pH 6.0 Specimen denaturation composition II: 20% EC, 10 mM citrate buffer, pH 6.0

Specimen denaturation composition III: 25% EC, 10 mM citrate buffer, pH 6.0

Specimen denaturation composition IV: 30% EC, 10 mM citrate buffer, pH 6.0

Specimen denaturation composition V: 40% EC, 10 mM citrate buffer, pH 6.0

Specimen denaturation composition VI: 40% EC

Specimen denaturation composition VII: 15% EC, 20% dextran sulfate; 600 mM NaCl; 10 mM citrate buffer, pH 6.0.

All six buffer compositions above stay in one phase at room temperature.

FISH Probe Composition: 2.5 ng/µL HER2 TxRed labeled DNA probe (¼ of standard concentration) and ½ of the standard concentration (300 nM) of CEN17 PNA probes; 15% EC, 20% dextran sulfate; 600 mM NaCl; 10 mM citrate buffer, pH 6.0.

The probe buffer was denatured at 82° C. for 5 min. The tissue samples were denatured with the different Specimen denaturation compositions at 82° C. for 5 min.

The slides were pre-treated as described above until the first dehydration step. After the samples had been digested with pepsin, the slides were washed 2×3 min, and 200 μL of one of the specimen denaturation compositions was added. The slides were then covered with a coverglass and incubated on a Hybridizer (Dako) at 82° C. for 5 min. The coverglass was then removed, and the slides were washed 2×3 mM in Wash Buffer, except for the slide with Specimen denaturation composition I*, which was washed in 2×SSC. The slides were then dehydrated in 96% ethanol for 2 min. and air-dried.

The FISH probe was denatured on a heat block in a 1.5 mL centrifuge tube at 82° C. for 5 min., and then put on ice. Ten μL of the denatured FISH probe was added to the denatured dehydrated specimen, the slides were coverslipped and sealed, and then hybridized at 45° C. for 60 min. Following hybridization, the specimens were treated as described above.

In the reference sample, the FISH probe and tissue were denatured together.

Results:

| Specimen denaturation buffer | Background | Signal Intensity | |
|---|---|---|---|
| | | DNA | PNA |
| I | +0-½ | 3 | 3 |
| I* | +0-½ | 3 | 3 |
| II | +0-½ | 3 | 3 |
| III | +½ | 3 | 3 |
| IV | +½-1 | 3 | 3 |
| V | +½-1 | 3 | 3 |
| VI | +1 | 3 | 3 |
| VII | +½ | 3 | 3 |
| Reference | +2 | 3 | 3 |

*This slide was washed with 2x SSC for 2 × 3 min., instead of Wash Buffer, after denaturation and dehydration before probe application, and showed slightly increased background staining compared to the corresponding slide washed with Wash Buffer.

These results show that separate denaturation of the sample and the probe significantly reduces background compared to co-denaturation of the probe and the specimen. The background staining also was more homogenous than when the probe and specimen were co-denatured (data not shown).

Example 25

This example compares signal intensity and background for experiments involving co-denaturation of the probe and specimen before hybridization, and experiments involving separate denaturation of the probe and specimen before hybridization.

FISH Probe Composition: 2.5 ng/μL HER2 TxRed labeled DNA probe (¼ of standard concentration) and ½ of the standard concentration (300 nM) of CEN17 PNA probes; 15% EC, 20% dextran sulfate; 600 mM NaCl; 10 mM citrate buffer, pH 6.0.

Specimen denaturation composition: 15% EC, 20% dextran sulfate; 600 mM NaCl; 10 mM citrate buffer, pH 6.0.

The slides were pre-treated as described above until the first dehydration step. After the samples had been digested with pepsin, the slides were washed 2×3 min, and 200 μL of the specimen denaturation composition was added. The slides were covered with a coverglass and incubated on a Hybridizer (Dako) at 72° C. for 10 min. The coverglass was then removed, and the slides were washed 2×3 min, dehydrated in 96% ethanol for 2 min., and air-dried.

The FISH probe (aliquots of 11 μL) was denatured on a heat block in 1.5 mL centrifuge tubes as indicated in the table and then put on ice. Ten μL of the denatured FISH probe was added to the denatured dehydrated specimen. The slides were coverslipped and sealed, and hybridized at 45° C. for 60 min. Following hybridization, the specimens were treated as described above.

Results:

| Probe denaturation temp | Probe denaturation time | Background | Signal Intensity | |
|---|---|---|---|---|
| | | | DNA | PNA |
| 62° C. | 1 min | +0-½ | 3 | 3 |
| 62° C. | 3 min | +0-½ | 3 | 3 |
| 62° C. | 5 min | +0-½ | 3 | 3 |
| 62° C. | 10 min | +0-½ | 3 | 3 |
| 72° C. | 1 min | +0-½ | 3 | 3 |
| 72° C. | 3 min | +0-½ | 3 | 3 |
| 72° C. | 5 min | +0-½ | 3 | 3 |
| 72° C. | 10 min | +0-½ | 3 | 3 |

These results show that it is possible to lower the denaturation temperature of the FISH probe to, e.g., 62° C. for 1 min. without negatively impacting the signal intensity or background.

Example 26

This example compares signal intensity and background for experiments involving co-denaturation of the probe and specimen before hybridization, and experiments involving separate denaturation of the probe and specimen before hybridization. FISH Probe Composition I: 2.5 ng/μL HER2 TxRed labeled DNA probe (¼ of standard concentration) and ½ of the standard concentration (300 nM) of CEN17 PNA probes; 15% EC, 20% dextran sulfate; 600 mM NaCl; 10 mM citrate buffer, pH 6.2.

Specimen denaturation composition II: 15% EC, 10 mM citrate buffer, pH 6.2.

Specimen denaturation composition III: 15% EC, 20% dextran sulfate; 600 mM NaCl; 10 mM citrate buffer, pH 6.2.

The slides were pre-treated as described above until the denaturation step. After the samples had been dehydrated, 200 μL of the specimen denaturation composition was added. The slides were covered with a coverglass and incubated on a Hybridizer (Dako) at 67° C. for 10 min. The coverglass was then removed, and the slides were washed 2×3 min, dehydrated in 96% ethanol for 2 min, and air-dried.

The FISH probe was denatured on a heat block in 1.5 mL centrifuge tubes at 67° C. for 3 min and used immediately after. Ten μL of the denatured FISH probe was added to the denatured dehydrated specimen. The slides were coverslipped and sealed, and hybridized at 45° C. for 60 min. Following hybridization, the specimens were treated as described above.

In the reference sample, the FISH probe and tissue were denatured together at 67° C. for 10 min and hybridized at 45° C. for 60 min.

Results:

| Probe denaturation | Tissue denaturation | Background | Signal Intensity | |
|---|---|---|---|---|
| | | | DNA | PNA |
| I | II | +0 | 3 | 3 |
| I | III | +½-1 | 3 | 3 |
| I (reference) | | +2 | 3 | 3 |

These results show that separate denaturation of the sample and the probe significantly reduced background compared to co-denaturation of the probe and the specimen. The background staining also was more homogenous than when the probe and specimen were co-denatured. The background staining is slightly lower when the denaturation buffer does not contain dextran sulfate and NaCl.

Example 27

This example compares signal intensity and background for experiments involving co-denaturation of the probe and specimen before hybridization, and experiments involving separate denaturation of the probe and specimen each with different denaturation agents before hybridization.

FISH Probe Composition I: 40% formamide, 10% dextran sulfate, 300 mM NaCl, 5 mM phosphate buffer, 5 µM blocking PNAs, 10 ng/µL HER2 TxRed labeled DNA gene probe standard concentration (600 mM) of CEN17 PNA probes.

Specimen denaturation composition II: 40% formamide, 10% dextran sulfate, 300 mM NaCl, 5 mM phosphate buffer, 5 µM blocking PNAs.

Specimen denaturation composition III: 15% EC, 10 mM citrate buffer, pH 6.2.

The slides were pre-treated as described above until the denaturation step. After the samples had been dehydrated, 100 µL of the specimen denaturation composition was added. The slides were covered with a coverglass and incubated on a Hybridizer (Dako) as indicated. The coverglass was then removed, and the slides were washed 2×3 min, dehydrated in 96% ethanol for 2 min., and air-dried.

The FISH probe was denatured on a heat block in 1.5 mL centrifuge tubes at 82° C. for 5 min and used immediately after. Ten µL of the denatured FISH probe was added to the denatured dehydrated specimen. The slides were coverslipped and sealed, and hybridized at 45° C. for overnight (about 20 h). Following hybridization, the specimens were treated as described above.

In the reference sample, the FISH probe and tissue were denatured together as indicated and hybridized at 45° C. for overnight (about 20 h).

Results:

| Probe denaturation | Tissue | Tissue denaturation temperature | Background | Signal Intensity | |
|---|---|---|---|---|---|
| | | | | DNA | PNA |
| 82° C./5 min | denaturation | | | | |
| I | II | 67° C./10 min | +½ | 2½ | 2 |
| I | II | 82° C./5 min | +½ | 2 | 2 |
| I | III | 67° C./10 min | +0 | 2½ | 2½ |
| I | III | 82° C./5 min | +0 | 2 | 2½ |
| I 67° C./10 min (co-denaturation) | | | +0 | 2 | 2½ |
| I (reference) 82° C./5 min (co-denaturation) | | | +0 | 2½ | 2½ |

These results show that separate denaturation of the sample with EC provides equivalent staining background and signal intensities, when compared to co-denaturation of the probe and the specimen with formamide. The DNA signal was though slightly stronger with EC (III) than formamide (II) at the lower denaturation temperature. The background staining was lower with specimen composition III (EC) than with specimen composition II (formamide). The best result for denaturation at 67° C./10 min for both separate and co-denaturation was obtained with separate denaturation using composition III (EC), which produced results equivalent to the reference.

Example 28

This example compares signal intensity and background for experiments involving separate denaturation of the probe and specimen before hybridization.

FISH Probe Composition I: 3.3 ng/µL HER2 TxRed labeled DNA probe (⅓ of standard concentration) and ½ of the standard concentration (300 nM) of CEN17 PNA probes; 15% EC (E26258, Aldrich-Sigma), 20% dextran sulfate; 600 mM NaCl; 10 mM citrate buffer, pH 6.2.

FISH Probe Composition II: 3.3 ng/µL HER2 TxRed labeled DNA probe (⅓ of standard concentration) and ½ of the standard concentration (300 nM) of CEN17 PNA probes; 15% SL, 20% dextran sulfate; 600 mM NaCl; 10 mM citrate buffer, pH 6.2.

FISH Probe Composition III: 3.3 ng/µL HER2 TxRed labeled DNA probe (⅓ of standard concentration) and ½ of the standard concentration (300 nM) of CEN17 PNA probes; 15% PC, 20% dextran sulfate; 600 mM NaCl; 10 mM citrate buffer, pH 6.2.

FISH Probe Composition IV: 3.3 ng/µL HER2 TxRed labeled DNA probe (⅓ of standard concentration) and ½ of the standard concentration (300 nM) of CEN17 PNA probes; 15% GBL, 20% dextran sulfate; 600 mM NaCl; 10 mM citrate buffer, pH 6.2.

FISH Probe Composition V: 3.3 ng/µL HER2 TxRed labeled DNA probe (⅓ of standard concentration) and ½ of the standard concentration (300 nM) of CEN17 PNA probes; 15% formamide, 20% dextran sulfate; 600 mM NaCl; 10 mM citrate buffer, pH 6.2.

Specimen denaturation composition VI: 15% EC, 10 mM citrate buffer, pH 6.2.

Specimen denaturation composition VII: 15% SL, 10 mM citrate buffer, pH 6.2.

Specimen denaturation composition VIII: 15% PC, 10 mM citrate buffer, pH 6.2.

Specimen denaturation composition IX: 15% GBL, 10 mM citrate buffer, pH 6.2.

Specimen denaturation composition X: 15% formamide, 10 mM citrate buffer, pH 6.2.

The slides were pre-treated as described above until the denaturation step. After the samples had been dehydrated, 200 µL of the specimen denaturation composition was added. The slides were covered with a coverglass and incubated on a Hybridizer (Dako) at 67° C. for 10 min. The coverglass was then removed, and the slides were washed 2×3 min, dehydrated in 96% ethanol for 2 min, and air-dried.

The FISH probe was denatured on a heat block in tubes at 67° C. for 5 min and used immediately after. Ten µL of the denatured FISH probe was added to the denatured dehydrated specimen. The slides were coverslipped and sealed, and hybridized at 45° C. for 60 min. Following hybridization, the specimens were treated as described above.

| Probe denaturation | Tissue denaturation | Background | Signal Intensity | |
|---|---|---|---|---|
| | | | DNA | PNA |
| I (EC) | VI (EC) | +½ | 3 | 3 |
| II (SL) | VII (SL) | +½ | 1½ | 2½ |
| III (PC) | VIII (PC) | +2 | 2 | 3 |
| IV (GBL) | IX (GBL) | +2 | 3 | 3 |
| V (formamide) | X (formamide) | +½ | 0 | 3 |

These results show that separate denaturation with EC, SL, PC and GBL provide stronger signals intensities for DNA probes, compared to separate denaturation with formamide when using short hybridization incubation time (60 min).

Example 29

This example compares signal intensity and background for experiments involving separate denaturation of the probe and specimen before hybridization.

FISH Probe Composition I: 3.3 ng/μL HER2 TxRed labeled DNA probe (⅓ of standard concentration) and ½ of the standard concentration (300 nM) of CEN17 PNA probes; 15% EC (E26258, Aldrich-Sigma), 20% dextran sulfate; 600 mM NaCl; 10 mM citrate buffer, pH 6.2.

Specimen denaturation composition II: 15% EC, 10 mM citrate buffer, pH 6.2.

Specimen denaturation composition III: 15% SL, 10 mM citrate buffer, pH 6.2.

Specimen denaturation composition IV: 15% PC, 10 mM citrate buffer, pH 6.2.

Specimen denaturation composition V: 15% GBL, 10 mM citrate buffer, pH 6.2.

Specimen denaturation composition VI: 15% formamide, 10 mM citrate buffer, pH 6.2.

The slides were pre-treated as described above until the denaturation step. After the samples had been dehydrated, 200 μL of the specimen denaturation composition was added. The slides were covered with a coverglass and incubated on a Hybridizer (Dako) at 67° C. for 10 min. The coverglass was then removed, and the slides were washed 2×3 min, dehydrated in 96% ethanol for 2 min., and air-dried.

The FISH probe was denatured on a heat block in tubes at 67° C. for 5 min and used immediately after. Ten μL of the denatured FISH probe was added to the denatured dehydrated specimen. The slides were coverslipped and sealed, and hybridized at 45° C. for 60 min. Following hybridization, the specimens were treated as described above.

| Probe denaturation | Tissue denaturation | Background | Signal Intensity DNA | PNA |
|---|---|---|---|---|
| I (EC) | II (EC) | +1 | 2½ | 3 |
| I (EC) | III (SL) | +1-1½ | 2½-3 | 3 |
| I (EC) | IV (PC) | +1 | 2½-3 | 3 |
| I (EC) | V (GBL) | +1 | 3 | 3 |
| I (EC) | VI (formamide) | +1 | 3 | 3 |

These results show that separate denaturation of tissue with EC (II), SL (III), PC (IV), GBL (V) and formamide (VI) provides equivalent staining background and signal intensities when using a polar aprotic based probe buffer (I) and short hybridization incubation time (60 min).

Example 30

This example compares signal intensity and background for experiments involving separate denaturation of the probe and specimen before hybridization.

FISH Probe Composition I (K5331, Dako): 40% formamide, 10% dextran sulfate, 300 mM NaCl, 5 mM phosphate buffer, 5 μM blocking PNAs, 10 ng/μL HER2 TxRed labeled DNA gene probe standard concentration (600 mM) of CEN17 PNA probes.

Specimen denaturation composition II: 15% EC, 10 mM citrate buffer, pH 6.2.

Specimen denaturation composition III: 15% SL, 10 mM citrate buffer, pH 6.2.

Specimen denaturation composition IV: 15% PC, 10 mM citrate buffer, pH 6.2.

Specimen denaturation composition V: 15% GBL, 10 mM citrate buffer, pH 6.2.

Specimen denaturation composition VI: 15% formamide, 10 mM citrate buffer, pH 6.2.

The slides were pre-treated as described above until the denaturation step. After the samples had been dehydrated, 200 μL of the specimen denaturation composition was added. The slides were covered with a coverglass and incubated on a Hybridizer (Dako) at 67° C. for 10 min. The coverglass was removed, and the slides were then washed 2×3 min, dehydrated in 96% ethanol for 2 min, and air-dried.

The FISH probe was denatured on a heat block in tubes at 82° C. for 5 min and used immediately after. Ten μL of the denatured FISH probe was added to the denatured dehydrated specimen. The slides were coverslipped and sealed, and hybridized at 45° C. overnight. Following hybridization, the specimens were treated as described above.

| Probe denaturation | Tissue denaturation | Background | Signal Intensity DNA | PNA |
|---|---|---|---|---|
| I (formamide) | II (EC) | +½ | 2 | 3 |
| I (formamide) | III (SL) | +½ | 1½ | 3 |
| I (formamide) | IV (PC) | +½-1 | 3 | 3 |
| I (formamide) | V (GBL) | +½ | 2 | 3 |
| I (formamide) | VI (formamide) | +½ | 1½ | 3 |

These results show that separate tissue denaturation with EC (II), SL (III), PC (IV) and GBL (V) provide equivalent or better signal intensities, when compared to separate tissue denaturation with formamide (VI). This was true when using a pre-denaturated traditional formamide based probe (I) and long hybridization incubation time (about 20 h). The background staining was equivalent.

FURTHER EMBODIMENTS

Embodiment 1

A method of hybridizing nucleic acid sequences comprising:
  combining a first nucleic acid sequence with a first aqueous composition comprising at least one polar aprotic solvent in an amount effective to denature a double-stranded nucleotide sequence,
  combining a second nucleic acid sequence with a second aqueous composition comprising at least denaturing agent in an amount effective to denature double-stranded nucleotide sequence, and
  combining the first and the second nucleic acid sequence for at least a time period sufficient to hybridize the first and second nucleic acid sequences,
  wherein the polar aprotic solvent is not dimethyl sulfoxide (DMSO).

Embodiment 2

A method of hybridizing nucleic acid sequences comprising:
  combining a first nucleic acid sequence with a first aqueous composition comprising at least one polar aprotic solvent in an amount effective to denature a double-stranded nucleotide sequence, and combining said first nucleic acid sequence with a second aqueous composition comprising a second nucleic acid sequence and at least one denaturing agent in an amount effective to denature double-stranded nucleotide sequences for at least a time period sufficient to hybridize the first and second nucleic acid sequences, wherein the polar aprotic solvent is not dimethyl sulfoxide (DMSO).

Embodiment 3

A method of hybridizing nucleic acid sequences comprising:
combining a first nucleic acid sequence with a first aqueous composition comprising at least one polar aprotic solvent in an amount effective to denature a double-stranded nucleotide sequence, and
combining said first nucleic acid sequence with a second nucleic acid sequence for at least a time period sufficient to hybridize the first and second nucleic acid sequences,
wherein the polar aprotic solvent is not dimethyl sulfoxide (DMSO).

Embodiment 4

The method according to embodiments 1 or 2, wherein the denaturing agent in the second aqueous composition is a polar aprotic solvent.

Embodiment 5

The method according to any one of embodiments 1 to 4, wherein the first nucleic acid sequence is in a biological sample.

Embodiment 6

The method according to embodiment 5, wherein the biological sample is a cytology or histology sample.

Embodiment 7

The method according to any of embodiments 1-6, wherein the first nucleic acid sequence is a single stranded sequence and the second nucleic acid sequence is a double stranded sequence.

Embodiment 8

The method according to any of embodiments 1-6, wherein the first nucleic acid sequence is a double stranded sequence and the second nucleic acid sequence is a single stranded sequence.

Embodiment 9

The method according to any of embodiments 1-6, wherein the first and second nucleic acid sequences are double stranded sequences.

Embodiment 10

The method according to any of embodiments 1-6, wherein the first and second nucleic acid sequences are single stranded sequences.

Embodiment 11

The method according to any of embodiments 1-10, wherein a sufficient amount of energy to hybridize the first and second nucleic acids is provided.

Embodiment 12

The method according to any of embodiments 1-11, wherein a sufficient amount of energy to denature the first nucleic acid is provided.

Embodiment 13

The method according to any of embodiments 1-12, wherein a sufficient amount of energy to denature the second nucleic acid is provided.

Embodiment 14

The method according to embodiments 11-13, wherein the energy is provided by heating the compositions.

Embodiment 15

The method according to embodiment 14, wherein the heating step is performed by the use of microwaves, hot baths, hot plates, heat wire, peltier element, induction heating or heat lamps.

Embodiment 16

The method according to any one of embodiments 12-15, wherein the temperature for denaturing the first nucleic acid is 70° C. to 85° C.

Embodiment 17

The method according to any one of embodiments 12-16, wherein the temperature for denaturing the second nucleic acid is 70° C. to 85° C.

Embodiment 18

The method according to any one of embodiments 12-15, wherein the temperature for denaturing the first nucleic acid is 60° C. to 75° C.

Embodiment 19

The method according to any one of embodiments 12-15 or 18, wherein the temperature for denaturing the second nucleic acid is 60° C. to 75° C.

Embodiment 20

The method according to any one of embodiments 12-15, wherein the temperature for denaturing the first nucleic acid is 62° C., 67° C., 72° C., or 82° C.

Embodiment 21

The method according to any one of embodiments 12-15 or 20, wherein the temperature for denaturing the second nucleic acid is 62° C., 67° C., 72° C., or 82° C.

Embodiment 22

The method according to any of embodiments 1-21, wherein a sufficient amount of time to denature the first nucleic acid is provided.

Embodiment 23

The method according to any of embodiments 1-22, wherein a sufficient amount of time to denature the second nucleic acid is provided.

Embodiment 24

The method according to embodiment 22 or 23, wherein the time is 1 minute, 2 minutes, 3 minutes, 4 minutes, 5 minutes, 10 minutes, 15 minutes, or 30 minutes.

Embodiment 25

The method according to any one of embodiments 1-24, wherein the step of hybridizing includes the steps of heating and cooling the compositions.

Embodiment 26

The method according to any one of embodiments 1-25, wherein the step of hybridization takes less than 8 hours.

Embodiment 27

The method according to embodiment 26, wherein the step of hybridization takes less than 1 hour.

Embodiment 28

The method according to embodiment 27, wherein the step of hybridization takes less than 30 minutes.

Embodiment 29

The method according to embodiment 28, wherein the step of hybridization takes less than 15 minutes.

Embodiment 30

The method according to embodiment 29, wherein the step of hybridization takes less than 5 minutes.

Embodiment 31

The method according to any one of embodiments 1-30, further comprising a blocking step.

Embodiment 32

The method according to any one of embodiments 1-31, wherein the concentration of polar aprotic solvent in the aqueous composition(s) is about 1% to 95% (v/v).

Embodiment 33

The method according to embodiment 32, wherein the concentration of polar aprotic solvent is 5% to 10% (v/v).

Embodiment 34

The method according to embodiment 32, wherein the concentration of polar aprotic solvent is 10% to 20% (v/v).

Embodiment 35

The method according to embodiment 32, wherein the concentration of polar aprotic solvent is 20% to 30% (v/v).

Embodiment 36

The method according to any one of embodiments 1-35, wherein the polar aprotic solvent in the aqueous composition(s) is non-toxic.

Embodiment 37

The method according to any one of embodiments 1-36, with the proviso that the aqueous composition(s) do not contain formamide.

Embodiment 38

The method according to any one of embodiments 1-36, with the proviso that the aqueous composition(s) contain less than 10% formamide.

Embodiment 39

The method according to embodiment 38, with the proviso that the aqueous composition(s) contain less than 2% formamide.

Embodiment 40

The method according to embodiment 39, with the proviso that the aqueous composition(s) contains less than 1% formamide.

Embodiment 41

The method according to any of embodiments 1-40, wherein the polar aprotic solvent in the aqueous composition(s) has lactone, sulfone, nitrile, sulfite, and/or carbonate functionality.

Embodiment 42

The method according to any one of embodiments 1-41, wherein the polar aprotic solvent in the aqueous composition(s) has a dispersion solubility parameter between 17.7 to 22.0 $MPa^{1/2}$, a polar solubility parameter between 13 to 23 $MPa^{1/2}$, and a hydrogen bonding solubility parameter between 3 to 13 $MPa^{1/2}$.

Embodiment 43

The method according to any one of embodiments 1-42, wherein the polar aprotic solvent in the aqueous composition(s) has a cyclic base structure.

Embodiment 44

The method according to any one of embodiments 1-43, wherein the polar aprotic solvent in the aqueous composition(s) is selected from the group consisting of:

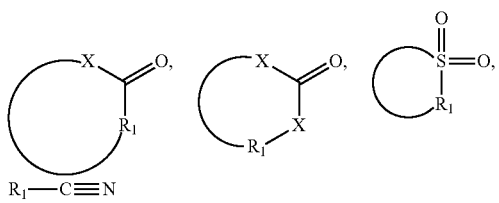

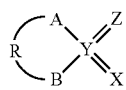

where X is O and R1 is alkyldiyl, and where X is optional and if present, is chosen from O or S,
where Z is optional and if present, is chosen from O or S,
where A and B independently are O or N or S or part of the alkyldiyl or a primary amine,
where R is alkyldiyl, and
where Y is O or S or C.

Embodiment 45

The method according to any one of embodiments 1-44, wherein the polar aprotic solvent in the aqueous composition(s) is selected from the group consisting of: acetanilide, acetonitrile, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, diphenynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

Embodiment 46

The method according to any one of embodiments 1-44, wherein the polar aprotic solvent in the aqueous composition(s) is:

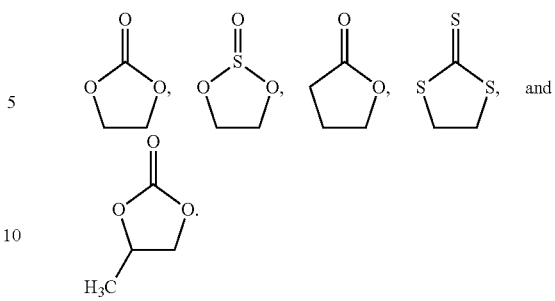

Embodiment 47

The method according to any one of embodiments 1-44, wherein the polar aprotic solvent in the aqueous composition(s) is:

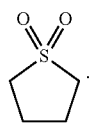

Embodiment 48

The method according to any one of embodiments 1-47, wherein the aqueous composition(s) further comprise at least one additional component selected from the group consisting of: buffering agents, salts, accelerating agents, chelating agents, detergents, and blocking agents.

Embodiment 49

The method according to embodiment 48, wherein the accelerating agent is dextran sulfate and the salts are NaCl and/or phosphate buffer.

Embodiment 50

The method according to embodiment 49, wherein the dextran sulfate is present at a concentration of 5% to 40%, the NaCl is present at a concentration of 0 mM to 1200 mM, and/or the phosphate buffer is present at a concentration of 0mM to 50 mM.

Embodiment 51

The method according to embodiment 50, wherein the dextran sulfate is present at a concentration of 10% to 30%, the NaCl is present at a concentration of 300 mM to 600 mM, and/or the phosphate buffer is present at a concentration of 5 mM to 20 mM.

Embodiment 52

The method according to embodiment 48, wherein the accelerating agent is selected from the group consisting of: formamide, DMSO, glycerol, propylene glycol, 1,2-propanediol, diethylene glycol, ethylene glycol, glycol, and 1,3 propanediol, and the buffering agent is citric acid buffer.

Embodiment 53

The method according to embodiment 52, wherein the formamide is present at a concentration of 0.1-5%, the DMSO is present at a concentration of 0.01% to 10%, the glycerol, propylene glycol, 1,2-propanediol, diethylene glycol, ethylene glycol, glycol, and 1,3 propanediol are present at a concentration of 0.1% to 10%, and the citric acid buffer is present at a concentration of 1 mM to 50 mM.

Embodiment 54

The method according to embodiment 48, wherein the blocking agent is selected from the group consisting of: total human DNA, herring sperm DNA, salmon sperm DNA, and calf thymus DNA.

Embodiment 55

The method according to embodiment 54, wherein the total human DNA, herring sperm DNA, salmon sperm DNA, and calf thymus DNA are present at a concentration of 0.01 to 10 µg/4.

Embodiment 56

The method according to embodiment 48, wherein the aqueous composition(s) comprise 40% of at least one polar aprotic solvent, 10% dextran sulfate, 300 mM NaCl, and/or 5 mM phosphate buffer.

Embodiment 57

The method according to embodiment 48, wherein the aqueous composition(s) comprise 15% of at least one polar aprotic solvent, 20% dextran sulfate, 600 mM NaCl, and/or 10 mM phosphate buffer.

Embodiment 58

The method according to embodiment 48, wherein the aqueous composition(s) comprise 15% of at least one polar aprotic solvent, 20% dextran sulfate, 600 mM NaCl, and 10 mM citric acid buffer pH 6.2.

Embodiment 59

The method according to any one of embodiments 1-58, wherein the aqueous composition(s) comprise one phase at room temperature.

Embodiment 60

The method according to any one of embodiments 1-58, wherein the aqueous composition(s) comprise multiple phases at room temperature.

Embodiment 61

The method according to embodiment 60, wherein the aqueous composition(s) comprise two phases at room temperature.

Embodiment 62

The method according to embodiment 60 or 61, wherein the phases of the aqueous composition(s) are mixed.

Embodiment 63

An aqueous composition for performing separate denaturation of a target in a hybridization application, said composition comprising at least one polar aprotic solvent in an amount effective to denature a double-stranded nucleotide sequence, wherein the polar aprotic solvent is not dimethyl sulfoxide (DMSO).

Embodiment 64

The aqueous composition of embodiment 63, wherein the concentration of polar aprotic solvent is defined as in any one of embodiments 32 to 35.

Embodiment 65

The aqueous composition of embodiment 63 or 64, wherein the polar aprotic solvent is defined as in any one of embodiments 36 or 41 to 47.

Embodiment 66

The aqueous composition of any one of embodiments 61 to 65, wherein the aqueous composition is defined as in any one of embodiments 37 to 40 or 48 to 62.

Embodiment 67

Use of a composition comprising between 1 and 95% (v/v) of at least one polar aprotic solvent for performing a separate denaturation of a target in a hybridization application.

Embodiment 68

Use of a composition according to embodiment 67, wherein the concentration of polar aprotic solvent is defined as in any one of embodiments 32 to 35.

Embodiment 69

Use of a composition according to embodiment 67 or 68, wherein the polar aprotic solvent is defined as in any one of embodiments 36 or 41 to 47.

Embodiment 70

Use of a composition according to any one of embodiments 67 to 69, wherein the aqueous composition is defined as in any one of embodiments 37 to 40 or 48 to 62.

Embodiment 71

A kit for performing a hybridization assay comprising:
- a first aqueous composition according to any one of embodiments 63-66; and
- a second aqueous composition comprising at least one nucleic acid sequence.

Embodiment 72

The kit according to embodiment 71, wherein the second aqueous composition further comprises at least one denaturing agent in an amount effective to denature double-stranded nucleotide sequences.

Embodiment 73

The kit according to embodiment 72, wherein the denaturing agent in the second aqueous composition is a polar aprotic solvent.

Embodiment 74

The kit according to embodiment 73, wherein the concentration of polar aprotic solvent in the second aqueous composition is defined as in any one of embodiments 32 to 35.

Embodiment 75

The kit according to embodiment 73 or 74, wherein the polar aprotic solvent in the second aqueous composition is defined as in any one of embodiments 36 or 41 to 47.

Embodiment 76

The kit according to any one of embodiments 71 to 75, wherein the second aqueous composition is defined as in any one of embodiments 37 to 40 or 48 to 62.

The invention claimed is:

1. A method of hybridizing nucleic acid sequences comprising:
    combining a first nucleic acid sequence with a first aqueous composition comprising at least one polar aprotic solvent in an amount effective to denature a double-stranded nucleotide sequence, and
    combining said first nucleic acid sequence with a second nucleic acid sequence for at least a time period sufficient to hybridize the first and second nucleic acid sequences,
    wherein the polar aprotic solvent is not dimethyl sulfoxide (DMSO).
2. The method according to claim 1, wherein the first nucleic acid sequence is in a biological sample.
3. The method according to claim 2, wherein the biological sample is a cytology or histology sample.
4. The method according to claim 1, wherein (a) a sufficient amount of energy to hybridize the first and second nucleic acids is provided; (b) a sufficient amount of energy to denature the first nucleic acid is provided; and/or (c) a sufficient amount of energy to denature the second nucleic acid is provided.
5. The method according to claim 1, wherein the step of hybridization takes less than 8 hours.
6. The method according to claim 1, wherein the step of hybridization takes less than 1 hour.
7. The method according to claim 1, with the proviso that the aqueous composition does not contain formamide.
8. The method according to claim 1, with the proviso that the first aqueous composition contain less than 10% formamide.
9. The method according to claim 1, wherein the polar aprotic solvent in the first aqueous composition has lactone, sulfone, nitrile, sulfite, and/or carbonate functionality.
10. The method according to claim 9, wherein the polar aprotic solvent in the first aqueous composition has a cyclic base structure.
11. The method according to claim 9, wherein the polar aprotic solvent in the first aqueous composition is selected from the group consisting of:

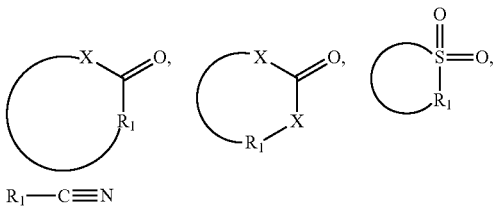

where X is O and R1 is alkyldiyl, and

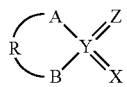

where X is optional and if present, is chosen from O or S, where Z is optional and if present, is chosen from O or S, where A and B independently are O or N or S or part of the alkyldiyl or a primary amine, where R is alkyldiyl, and where Y is O or S or C.

12. The method according to claim 1, wherein the polar aprotic solvent in the first aqueous composition is selected from the group consisting of: acetanilide, acetonitrile, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, dipheynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

13. The method according to claim 1, wherein the polar aprotic solvent in the first aqueous composition is selected from the group consisting of:

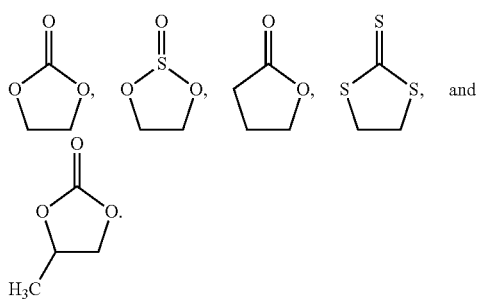

14. The method according to claim 1, wherein the polar aprotic solvent in the first aqueous composition is:

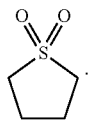

15. The method according to claim 1, wherein the first aqueous composition further comprise at least one additional component selected from the group consisting of: buffering agents, salts, accelerating agents, chelating agents, detergents, and blocking agents.

16. The method according to claim 15, wherein the accelerating agent is dextran sulfate and the salts are NaCl and/or phosphate buffer.

17. The method according to claim 16, wherein the dextran sulfate is present at a concentration of 5% to 40%, the NaCl is present at a concentration of 0 mM to 1200 mM, and/or the phosphate buffer is present at a concentration of 0 mM to 50 mM.

18. The method according to claim 17, wherein the dextran sulfate is present at a concentration of 10% to 30%, the NaCl is present at a concentration of 300 mM to 600 mM, and/or the phosphate buffer is present at a concentration of 5 mM to 20 mM.

19. The method according to claim 15, wherein the accelerating agent is selected from the group consisting of: formamide, DMSO, glycerol, propylene glycol, 1,2-propanediol, diethylene glycol, ethylene glycol, glycol, and 1,3 propanediol, and the buffering agent is citric acid buffer.

20. The method according to claim 19, wherein the formamide is present at a concentration of 0.1-5%, the DMSO is present at a concentration of 0.01% to 10%, the glycerol, propylene glycol, 1,2-propanediol, diethylene glycol, ethylene glycol, glycol, and 1,3 propanediol are present at a concentration of 0.1% to 10%, and the citric acid buffer is present at a concentration of 1 mM to 50 mM.

* * * * *

UNITED STATES PATENT AND TRADEMARK OFFICE
CERTIFICATE OF CORRECTION

PATENT NO. : 10,202,638 B2  
APPLICATION NO. : 15/096036  
DATED : February 12, 2019  
INVENTOR(S) : Steen Hauge Matthiesen Page 1 of 1

It is certified that error appears in the above-identified patent and that said Letters Patent is hereby corrected as shown below:

On the Title Page

Item [63], under Related U.S. Application Data, after "Pat. No. 9,309,562" insert -- , provisional application No. 61/289,617, filed Dec. 23, 2009, and provisional application No. 61/155,683, filed Feb. 26, 2009. --

Signed and Sealed this  
Ninth Day of July, 2019

Andrei Iancu  
*Director of the United States Patent and Trademark Office*